United States Patent
Helson

(10) Patent No.: US 10,117,881 B2
(45) Date of Patent: *Nov. 6, 2018

(54) PROTECTIVE EFFECT OF DMPC, DMPG, DMPC/DMPG, LYSOPG AND LYSOPC AGAINST DRUGS THAT CAUSE CHANNELOPATHIES

(71) Applicant: SignPath Pharma Inc., Quakertown, PA (US)

(72) Inventor: Lawrence Helson, Quakertown, PA (US)

(73) Assignee: Signpath Pharma, Inc., Sandy, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/347,381

(22) Filed: Nov. 9, 2016

(65) Prior Publication Data

US 2017/0095489 A1 Apr. 6, 2017

Related U.S. Application Data

(63) Continuation-in-part of application No. 15/068,300, filed on Mar. 11, 2016, which is a continuation of application No. 14/268,376, filed on May 2, 2014, now Pat. No. 9,682,041, which is a continuation of application No. 13/487,233, filed on Jun. 3, 2012, now Pat. No. 8,753,674, application No. 15/347,381, filed on Nov. 9, 2016, which is a continuation-in-part of application No. 14/575,644, filed on Dec. 18, 2014, and a continuation-in-part of application No. 14/729,940, filed on Jun. 3, 2015.

(60) Provisional application No. 61/493,257, filed on Jun. 3, 2011, provisional application No. 61/917,426, filed on Dec. 18, 2013, provisional application No. 61/977,417, filed on Apr. 9, 2014, provisional application No. 62/007,244, filed on Jun. 3, 2014, provisional application No. 62/035,417, filed on Aug. 9, 2014, provisional application No. 62/056,957, filed on Sep. 29, 2014, provisional application No. 62/150,059, filed on Apr. 20, 2015.

(51) Int. Cl.

| | | |
|---|---|---|
| *A61K 31/506* | (2006.01) | |
| *A61K 31/683* | (2006.01) | |
| *A61K 9/127* | (2006.01) | |
| *A61K 31/445* | (2006.01) | |
| *A61K 31/685* | (2006.01) | |
| *G01N 33/50* | (2006.01) | |

(52) U.S. Cl.

CPC ............ *A61K 31/683* (2013.01); *A61K 9/127* (2013.01); *A61K 31/445* (2013.01); *A61K 31/506* (2013.01); *A61K 31/685* (2013.01); *G01N 33/5088* (2013.01); *G01N 2800/326* (2013.01)

(58) Field of Classification Search
None
See application file for complete search history.

(56) References Cited

U.S. PATENT DOCUMENTS

| | | |
|---|---|---|
| 4,812,312 A | 3/1989 | Lopez-Berestein et al. |
| 5,023,087 A | 6/1991 | Yau-Young |
| 5,679,864 A | 10/1997 | Krackov et al. |
| 6,143,276 A | 11/2000 | Unger |
| 6,787,132 B1 | 9/2004 | Gabison et al. |
| 6,946,475 B1 | 9/2005 | Lloyd |
| 7,060,733 B2 | 6/2006 | Pandol et al. |
| 7,067,159 B2 | 6/2006 | Katz et al. |
| 7,507,864 B2 | 3/2009 | Miller et al. |
| 7,674,820 B2 | 3/2010 | Fedida et al. |
| 7,723,515 B1 | 5/2010 | DiMauro |
| 7,871,609 B2 | 1/2011 | Ziff et al. |
| 7,968,115 B2 | 6/2011 | Kurzrock et al. |
| 8,062,663 B2 | 11/2011 | Wang et al. |
| 8,153,172 B2 | 4/2012 | Antony |
| 8,202,839 B1 | 6/2012 | Sung |
| 8,207,219 B2 | 6/2012 | Fedida et al. |
| 8,642,074 B2 | 2/2014 | Mei et al. |
| 8,747,890 B2 | 6/2014 | Helson |
| 8,753,674 B2 | 6/2014 | Helson |
| 9,138,411 B2 | 9/2015 | Ranjan et al. |
| 2001/0051184 A1 | 12/2001 | Heng |
| 2002/0048598 A1 | 4/2002 | Malik |

(Continued)

FOREIGN PATENT DOCUMENTS

| | | |
|---|---|---|
| CA | 2584279 A1 | 4/2005 |
| CN | 104758255 | 7/2015 |

(Continued)

OTHER PUBLICATIONS

Vicenzi F, Citalopram-induced long QT syndrome and the mammalian dive reflex, Drug Saf—Case Rep, 2015, 2(12), pp. 1-5.*

(Continued)

*Primary Examiner* — Celeste A Roney

(74) *Attorney, Agent, or Firm* — Edwin S. Flores; Chalker Flores LLP

(57) ABSTRACT

The present invention includes compositions and methods for preventing one or more cardiac channelopathies or conditions resulting from irregularities or alterations in cardiac patterns caused by an active agent or a drug in a human or animal subject comprising: an amount of a lysophosphatidylglycerol adapted for oral administration effective to reduce or prevent one or more cardiac channelopathies or conditions resulting from irregularities or alterations in cardiac patterns caused by the active agent or drug.

18 Claims, 5 Drawing Sheets

(56) References Cited

U.S. PATENT DOCUMENTS

| | | |
|---|---|---|
| 2002/0110586 A1 | 8/2002 | Madden et al. |
| 2005/0101674 A1 | 5/2005 | Maurer et al. |
| 2005/0181036 A1 | 8/2005 | Aggarwal et al. |
| 2005/0233970 A1 | 10/2005 | Garnick |
| 2005/0266067 A1 | 12/2005 | Sengupta et al. |
| 2006/0067998 A1 | 3/2006 | Kurzrock et al. |
| 2006/0147512 A1 | 7/2006 | Sabin |
| 2006/0269595 A1* | 11/2006 | Madden ............... A61K 9/0019 424/450 |
| 2007/0048284 A1 | 3/2007 | Donahue et al. |
| 2008/0075671 A1 | 3/2008 | Di Mauro |
| 2008/0103213 A1 | 5/2008 | Kurzrock et al. |
| 2008/0107749 A1 | 5/2008 | Maitra et al. |
| 2008/0138400 A1 | 6/2008 | Kurzrock et al. |
| 2008/0253961 A1 | 10/2008 | Braden et al. |
| 2008/0255464 A1 | 10/2008 | Vincent |
| 2009/0143433 A1 | 6/2009 | Hendrix |
| 2009/0246770 A1 | 10/2009 | Levy |
| 2009/0291134 A1* | 11/2009 | Ahmad ............... A61K 9/06 424/463 |
| 2009/0317387 A1 | 12/2009 | Paton et al. |
| 2009/0324703 A1 | 12/2009 | Frautschy et al. |
| 2010/0004549 A1 | 1/2010 | Kohls et al. |
| 2010/0048957 A1 | 2/2010 | Kim |
| 2010/0068251 A1 | 3/2010 | Ali et al. |
| 2010/0093873 A1 | 4/2010 | Goldfischer |
| 2010/0120890 A1 | 5/2010 | Fedida |
| 2010/0151000 A1 | 6/2010 | Thomas et al. |
| 2010/0179103 A1 | 7/2010 | Desai |
| 2010/0239552 A1 | 9/2010 | Mayoux et al. |
| 2010/0240581 A1 | 9/2010 | Tortoriello et al. |
| 2010/0291043 A1 | 11/2010 | Medin et al. |
| 2011/0117186 A1 | 5/2011 | Helson |
| 2011/0229555 A1 | 9/2011 | Helson et al. |
| 2011/0287085 A1 | 11/2011 | Kurzrock et al. |
| 2012/0021036 A1 | 1/2012 | Majeti et al. |
| 2012/0031777 A1 | 2/2012 | Burke et al. |
| 2012/0058208 A1 | 3/2012 | Jacob |
| 2012/0237590 A1 | 9/2012 | Helson |
| 2012/0308643 A1 | 12/2012 | Helson |
| 2013/0310351 A1 | 11/2013 | Milan et al. |
| 2013/0337488 A1 | 12/2013 | Helson |
| 2014/0050780 A1 | 2/2014 | Cerundolo et al. |
| 2015/0164878 A1 | 6/2015 | Helson |
| 2015/0343063 A1 | 12/2015 | Helson |
| 2016/0193149 A1 | 7/2016 | Helson |
| 2017/0035887 A1 | 2/2017 | Helson |
| 2017/0119802 A1 | 5/2017 | Helson |
| 2017/0246110 A1 | 8/2017 | Helson |
| 2017/0312366 A1 | 11/2017 | Helson |
| 2018/0055770 A1 | 3/2018 | Helson |

FOREIGN PATENT DOCUMENTS

| | | |
|---|---|---|
| DE | 10029770 A1 | 12/2001 |
| EP | 3144006 | 3/2017 |
| JP | 10-279487 A | 10/1998 |
| JP | H10-191927 A | 7/2010 |
| WO | 2000070949 A1 | 11/2000 |
| WO | 2001093683 A1 | 12/2001 |
| WO | 2002002582 A1 | 1/2002 |
| WO | 2004047717 A2 | 6/2004 |
| WO | 2004080396 A2 | 9/2004 |
| WO | 2006061101 A2 | 6/2006 |
| WO | 2006131737 A2 | 12/2006 |
| WO | 2007062028 A2 | 5/2007 |
| WO | 2007103435 A2 | 9/2007 |
| WO | 2007129062 A1 | 11/2007 |
| WO | 2008045534 A2 | 4/2008 |
| WO | 2008063513 A2 | 5/2008 |
| WO | 2008128123 A2 | 10/2008 |
| WO | 2009051837 A2 | 4/2009 |
| WO | 2009073050 | 6/2009 |
| WO | 2010009186 A1 | 1/2010 |
| WO | 2010033692 A1 | 3/2010 |
| WO | 2010057332 A1 | 5/2010 |
| WO | 2011063178 A2 | 5/2011 |
| WO | 2011001351 A1 | 6/2011 |
| WO | 2011119588 A1 | 9/2011 |
| WO | 2012125830 A2 | 9/2012 |
| WO | 2012167212 A2 | 12/2012 |
| WO | 2013041894 | 3/2013 |
| WO | 2013166249 A1 | 11/2013 |
| WO | 2013188767 | 12/2013 |
| WO | 2013188767 A1 | 12/2013 |
| WO | 2015095576 A1 | 6/2015 |

OTHER PUBLICATIONS

Etheridge, SP, et al., "A New Oral Therapy for Long QT Syndrome: Long Term Oral Potassium Improves Repolarization in Patients with hERG Mutations," J Am Coll Cardiol, 2003; 42:1777-1782.

Everett, Peter C., et al., "Preclinical Assessment of Curcumin as a Potential Therapy for B-CLL," American Journal of Hematology, (2006), 8 pages.

Fahn, Stanlex, "Medical Treatment of Parkinson's Disease," Journal of Neurology, 1998, 245 (Supplement 3): P15-P24.

Fauchier, L, et al.,"JP: Effect of Verapamil on QT Interval Dynamicity," Am J Cardiol., 1999; 83(5):807-808 A10-1.

FDA Pharmacology Review of Xalkori (crizotinib), IND No. 202570, 2011a, www.accessdata.fda.gov/drugsatfda_docs/nda/2011/202570Orig1s000PharmR.pdf (accessed Oct. 9, 2013).

FDA Pharmacology of Tasigna® (nilotinib), IND No. 22-068, 2007a, www.accessdata.fda.gov/drugsatfda_docs/nda/2007/022068s000_PharmR_P1.pdf and www.accessdata.fda.gov/drugsatfda_docs/nda/2007/022068s000_MedR_P2.pdf, (accessed Oct. 25, 2013).

FOWLER, NO, et al., "Electrocardiographic Changes and Cardiac Arrhythmias in Patients Receiving Psychotropic Drugs," Am J Cardiol, 1976; 37(2):223-230.

Garcia-Alloza, M., et al., "Curcumin Labels Amyloid Pathology in Vivo, Disrupts Existing Plaques, and Partially Restroes distorterneurites in an Alzheimer Mouse Model," Journal of Neurochemistry, (2007), vol. 102, pp. 1095-1104.

Grama, C.N., et al., "Poly(lactide-glycolide) nanoparticles for peroral delivery of bioactives," Current Opinion in Colloid and Interface Science, London, GB, vol. 16, No. 3, Nov. 24, 2010, pp. 238-245.

Gukovsky, Ilya, et al., "Curcumin Ameliorates Ethanol and Nonethanol Experimental Pancreatitis," Am. J. Physiol. Gastrointest. Liver Physio., (2003), 284:G85-G95.

Harish, G., et al., "Bioconjugates of curcumin display improved protection against glutathione depletion mediated oxidative stress in a dopaminergic neuronal cell line: Implications for Parkinson's disease," Bioorgaic & Medicinal Chemistry, vol. 18, Feb. 20, 2010, pp. 2631-2638.

Helson, et al., "Liposome mitigation of curcumin inhibition of cardiac potassium delayed-rectifier current," Journal of Receptor, Ligand and Channel Research, Nov. 15, 2012, vol. 5, pp. 108.

Hernandez-Fonseca , Juan P., et al., "Structural and Ultrastructural Analysis of Cerebral Cortex, Cerebellum, and Hypothalamus from Diabetic Rats," Experimental Diabetes Research Oct. 1, 2009: 2009: 329632.

Jacob, Asha, et al., "Mechanism of the Anti-Inflammatory Effect of Curcumin: PPAR-y Activation," Hindawi Publishing Corporation, PPAR Research, (2007), Article ID 89369, 5 pages.

Jervell, A, et al., "Congenital Deaf-Mutism, Functional Heart Disease with Prolongation of the QT Interval and Sudden Death," Am Heart J., 1957; 54(1):59-68.

Kang, J, et al., "Discovery of a Small Molecule Activator of the Human Ether-a-go-go—Related Gene(HERG) Cardiac K+ Channel," Mol Pharmacol, 2005(3); 67:827-836.

Katchman, AN, et al., "Comparative Evaluation of HERG Currents and QT Intervals Following Challenge with Suspected Torsadogenic and Nontorsdogenic Drugs," J Pharmacol Exp Ther., 2006; 316(3):1098-1106.

Kessler, Ronald C., et al., "Posttraumatic Stress Disorder in the national Comorbidity Survey," Archives of General Psychiatry, vol. 52, No. 12, pp. 1049-1060.

(56) References Cited

OTHER PUBLICATIONS

Kim, K-P, et al., "Nilotinib in Patients with GIST who failed imatinib and sunitinib: importance of prior surgery on drug bioavailability," Jul. 12, 2010, Cancer Chemother. Pharmacol., vol. 68, pp. 285-291.

Kim, So Jung, et al., "Curumin Stimulates Proliferation of Embryonic Neural Progenitor Cells and Neurogenesis in the Adult Hippocampus," The Journal of Biological Chemistry, May 23, 2008, vol. 283, No. 21, pp. 14497-14505.

Koehler, Jacqueline A., et al., "Glucagon-Like Peptide-1 Receptor Activation Modulates Pancreatitis-Associated Gene Expression Bud Does Not Modify the Susceptibility to Experimental Pancreatitis in Mice," Diabetes, Sep. 2009, vol. 58, pp. 2148-2161.

Konwarh, R., et al., "Poly(ethylene glycol)-magnetic nanoparticles-curcumin trio: Directed morphogenesis and synergistic free-radical scavenging," Colloids and Surfaces B: Biointerfaces, vol. 81, Aug. 7, 2010, pp. 578-586.

Kourelis, Taxiarchis V., et al., "Metformin and Cancer: New Applications for an Old Drug," Med. Oncol., Feb. 8, 2011, 14 pages.

Kowluru, Renu A., et al., "Effects of Curcumin on Retinal Oxidative Stress and Inflammation in Diabetes," Nutrition & Metabolism, Apr. 16, 2007, 8 pages.

Kulkarni, S.K, et al., "An Overview of Curcumin in Neurological Disorders," Indian J. Pharm. Sci, Jul. 1, 2010, 72:2, pp. 149-154.

Kumar, T. Peeyush, et al., "Curcumin Modulates Dopaminergic Receptor, CREB and Phospholipase C Gene Expression in the Cerebral Cortex and Cerebellum of Streptozotocin Induced Diabetic Rats," Journal of Biomedical Science, (2010), 2:43, 11 pages.

Lamont, Benjamin J., et al., "Differential Antidiabetic Efficacy of Incretin Agonists Versus DPP-4 Inhibition in High Fat-Fed Mice," Diabetes, Jan. 2008, vol. 57, pp. 190-198.

Layton, D, et al., "Prolongation of the QT interval and cardiac arrhythmias associated with cisapride: limitations of the pharmacoepidemiological studies conducted and proposals for the future," Pharmacoepidemiol Drug Saf., 12(1), Nov. 13, 2002, pp. 31-40.

Lee, et al. "Electrophysiological Effects of the Anti-Cancer Drug Lapatinib on Cardiac Repolarization," Basic & Clinical Pharmacology & Toxicology, vol. 107, Dec. 21, 2009, pp. 614-618.

Leung, et al., "Effective stablization of curcumin by association to plasma proteins: human serum albumin and fibronogen," Langmuir, 2009, vol. 25, Issue 10, pp. 5773-5777.

Li, Yu-Cheng, et al., "Antidepressant-Like Effects of Curcumin on Serotonergic Receptor-Coupled Ac-cAMP Pathway in Chronic Unpredictable Mild Stress of Rats," Progress in Neuro-Psychophamacoloby & Biological Psychiatry, (2009), vol. 33, pp. 435-449.

Li, Lan, et al., "Liposome-Encapsulated Curcumin In Vitro and In Vivo Effects on Proliferation, Apoptosis, Signaling, and Angiogenesis," Cancer, May 4, 2005, 104:1322-1331.

Lim, Kah Jing, et al., "A Polymeric Nanoparticle Formulation of Curcumin Inhibits Growth, Clonogenicity and Stem-Like Fraction in Malignant Brain Tumors," Cancer Biology & Therapy, Mar. 1, 2011, 11:5, pp. 464-473.

Logan-Smith, Melanie J., et al., "Curcumin, a Molecule that Inhibits the Ca2+-ATPase of Sarcoplasmic Reticulum but Increases the Rate of Accumulation of Ca2+," The Journal of Biological Chemistry, (2001), vol. 276, No. 50, pp. 46905-46911.

Mach, Claire M., et al., "Determination of Minimum Effective Dose and Optimal Dosing Schedule for Liposomal Curcumin in a Xenograft Human Pancreatic Cancer Model," (2009), Anticancer Research, 29:1895-1900.

Maciel, NR, et al., "Reduced Cardiovascular Alterations of Tarter Emetic Administered in Long-Circulating Liposomes in Rats," Toxicology Letters, 2010; 199(3):234-238.

Marino, Silvia, et al., "Sertaline in the Treatment of Depressive Disorders in Patients with Parkinson's Disease," Neurological Sciences, Nov. 2008, 29:391-395.

Matsushita, Yuichi, et al., "Activation of Peroxisome Proliferator-Activated Receptor d Inhibits Streptozotocin-Induced Diabetic Nephropathy Through Anti-Inflammatory Mechanisms in Mice," Diabetes, Mar. 2011, vol. 60, pp. 960-968.

Mayer, Lawrence D., et al., "Intravenous Pretreatment with Empty pH Liposomes Alters the Pharmacokinetics and Toxicity of Doxorubicin through In Vivo Active Drug Encapsulation," Journal of Pharmaceutical Sciences, vol. 88, No. 1, Nov. 25, 1998, pp. 96-102.

Mehta, RT, et al., "Formulation, toxicity, and antifungal activity in vitro of liposomal-encapsulated nystatin as therapeutic agent for systemic candidiasis," Antimicrob Agents Chemother, 31(12), Dec. 1987, pp. 1897-1900.

Mishra, S., et al., "The effect of curcumin (turmeric) on Alzheimer's disease: An overview," Annals of Indian Academy of Neurology, vol. 11:1, 2008, pp. 13-19.

Moha, H, et al., "Curcumin blocks the recombinant human cardiac KCNQ 1/KCNE 1 channels (IKs) stably expressed in HEK 293 cells," Abstract of 12th Annual Meeting of the French Society of Pharmacology and Therapeutics, Fund. & Clin. Pharma., vol. 22:1, Jun. 2008.

Mosse, et al., "Safety and activity of crizotinib for pediatric patients with refractory solid tumours of anaplastic large-cell lymphoma: A Children's Oncology Group phase 1 consortium study," Lancet Oncol., May 2013, vol. 14(6), pp. 472-480.

Mukerjee, Anindita, et al., "Formulation, Characterization and Evaluation of Curcumin-Loaded PLGA Nanospheres for Cancer Therapy," (2009), Anticancer Research 29:3867-3876.

Murphy, Eric, A., et al., "Targeted Nanogels: A Versatile Platform for Drug Delivery to Tumors," Molecular Cancer Therapeutics, Apr. 25, 2011; 10:972-982.

Nam, et al., "Curcumin-Loaded PLGA Nanoparticles Coating onto Metal Stent by Electrophoretic Deposition Techniques," Bull. Korean Chem. Soc., Jan. 2007, vol. 28, No. 3, pp. 397-402.

Narala, Venkata R., et al., "Curcumin is not a Ligand for Peroxisome Proliferator-Activated Receptor-Y," Gene Therm. Mol. Biol., Apr. 1, 2009, 13(1):20-25.

Naseem, et al., "Bupivacaine Extended Release Lipsome Injection Does not Prolong Qtc Interval in a Thorough QT/QTc Study in Healthy Volunteers," Journal of Clin. Pharma., 2012, vol. 52, pp. 1441-1447.

Nousiainen, T., et al., "QT dispersion and late potentials during doxorubicin therapy for non-Hodgkin's lymphoma," Journal of Internal Medicine, 245, 1999, pp. 359-364.

Olansky, Leann, "Do Incretin-Based Therapies Cause Acute Pancreatitis?" Journal of Diabetes Science and Technology, Jan. 2010, vol. 4, Issue 1, pp. 228-229.

Zhou, et al., "Correction of Defectrive Protein Trafficking of a Mutant HERG Potassium Channel in Human Long QT Syndrome," The Journal of Biological Chemistry, vol. 274:44, Oct. 29, 1999, pp. 31123-31126.

Pitman, Roger K., et al., "Conceptually Driven Pharmacologic Approaches to Acute Trauma," CNS Spectrums, Feb. 2005, vol. 10, No. 2, pp. 99-106.

Quan, Xiao-Qing, et al., "Increasing Gap Junction Coupling Reduces Transmural Dispersion of Repolarization and Prevents Torsade de Pointes in Rabbit LQT3 Model," J. Cardiovasc. Electrophysiol., vol. 18, Nov. 2007, pp. 1184-1189.

Rajamani, S., et al., "Drug-induced long QT syndrome: hERG K+ channel block and disruption of protein trafficking by fluoxetine and norfluoxetine," British Journal of Pharmacology, Sep. 11, 2006, vol. 149, pp. 481-489.

Rajeswari, A., et al., "Inhibition of monoamine oxidase-B by the polyphenolic compound, curcumin and its metabolite tetrahydrocurcumin, in a model of Parkinson's disease induced by MPTP neurodegeneration in mice," Inflammopharmacology, vol. 16, 2008, pp. 96-99.

Ranjan, A. P., et al, "Efficacy of Liposomal Curcumin in a Human Pancreatic Tumor Xenograft Model: Inhibition of Tumor Growth and Angiogenesis," Anticancer Research, vol. 33, Jul. 26, 2013, pp. 3603-3610.

Ravindran, J., et al., "Curcumin and Cancer Cells: How Many Ways Can Curry Kill Tumor Cells Selectively?," The AAPS Journal, vol. 11, No. 3, Jul. 10, 2009, pp. 495-510.

(56) References Cited

OTHER PUBLICATIONS

Roberts, A.N., et al., "Molecular and Functional Characterization of Amylin, a Peptide Associated with Type 2 Diabetes Mellitus," Proc. Natl. Acad. Sci. USA, Dec. 1989, vol. 86, pp. 9662-9666.
Rosi, S., et al., "Chemokine Receptor 5 Antagonist d-Ala-Peptide T-Amide Reduces Microglia and Astrocyte Activation Within the Hippocampus in a Neuroinflammatory Rat Model of Alzheimer's Disease," Neuroscience, (2005), vol. 134, pp. 671-676.
Rui, Pan, et al., "Curcumin Improves Learning and Memory Ability and its Neuroprotective Mechanism in Mice," Chin. Med. J., (2008), vol. 121, No. 9, pp. 832-839.
Rusinek, Henry, et al., "Hippocampal Blood Flow in Normal Aging Measured with Arterial Spin Lavelin at 3T," Magnetic Resonance in Medicine, (2011), 65:128-137.
Schena, Francesco P., et al., "Pathogenetic Mechanisms of Diabetic Nephropathy," J. Am. Soc. Nephrol., (2005), 16:S30-S33.
Segman, RH., et al., "Association Between the Dopamine Transporter Gene and Posttraumatic Stress Disorder," Molecular Psychiatry, (2002), vol. 7, pp. 903-907.
Segman, RH., et al., "Peripheral Blood Mononuclear Cell Gene Expression Profiles Identify Emergent Post-Traumatic Stress Disorder Among Trauma Survivors," Molecular Psychiatry, (2005), vol. 10, pp. 500-513.
Shah, et al., "Cardiovascular Safety of Tyrosine Kinase Inhibitors: With a Special Focus on Cardiac Repolarisation (QT Interval)," Drug Saf., Apr. 26, 2013, vol. 36, pp. 295-316.
Shaikh, J., et al, "Nanoparticle encapsulation improves oral bioavailability of curcumin by at least 9-fold when compared to curcumin administered with piperine as absorption enhancer," European Journal of Pharmaceutical Sciences, Elsevier, Amsterdam, NL, vol. 37, No. 3-4, Jun. 28, 2009, pp. 223-230.
Shimizu, Wataru, et al., "Sodium Channel Block with Mexiletine is Effective in Reducing Dispersion of Repolarization and Preventing Torsade de Pointes in LQT2 and LQT3 Models of the Long-QT Syndrome," vol. 96, Apr. 28, 1997, pp. 2038-2047.
Shimizu, Wataru, et al. "Effects of a K+ Channel Opener to Reduce Transmural Dispersion of Repolarization and Prevent Torsade de Pointes in LQT1, LQT2, and LQT3 Models of the Long-QT Syndrome," Circulation, 2000, 102:706-712.
Singh, Sonal, et al., "Long-Term Risk of Cardiovascular Events with Rosiglitazone," JAMA, Sep. 12, 2007, vol. 298, No. 10, pp. 1189-1195.
Smith, Judith A., et al., "Abstract A29: Development of Liiposomal Curcumin as a New Potential Anticancer Agent," Molecular Cancer Therapeutics, Dec. 2009, vol. 8, Issue 12, Supplement 1, 1 page.
Stansfeld, Phillip, J., et al., "Drug Block of the hERG Potassium Channel: Insight From Modeling," Proteins: Structure, Function and Bioinformatics, Apr. 19, 2007, 68:568-580.
Stein, Murray B., et al., "Genetic and Environmental Influences on Trauma Exposure and Posttraumatic Stress Disorder Symptoms: A Twin Study," Am. J. Psychiatry, Oct. 2002, vol. 159, No. 10, pp. 1675-1681.
Sun, M., et al., "Enhancement of transport of curcumin to brain in mice by poly(n-butylcyanoacrylate) nanoparticle," J. Nanopart Res., vol. 12, 2010, pp. 3111-3122.
Tasigna Package insert, Novartis Pharmaceuticals, Revised Sep. 2013.
Tonnesen, Hanne, H., et al, "Studies on curcumin and curcuminoids: XXV. Inhibition of primaquine-induced lysis of human red blood cells by curcumin," International Journal of Pharmaceutics 110 (1994) 161-167.
U.S. Department of Health and Human Services, "Guidance for Industry, S7B Nonclinical Evaluation of the Potential for Delayed Ventricular Repolarization (QT Interval Prolongation) by Human Pharmaceuticals," Oct. 2005, pp. 1-13.
Van De Water, et al., "An Improved Method to Correct the QT Interval of the Electrocardiogram for Changes in Heart Rate," Journal of Pharmacological Methods, Apr. 1989, vol. 22, pp. 207-217.

Verma, Richa, et al., "Structural and functional changes in a syntheitic S5 segment of KvLQT1 channel as a result of a conserved amino acid substitution that occurs in LQT1 syndrome of human," Biochimica et Biophysica Acta, 1798, Jan. 2010, pp. 461-470.
Vidal, Alessandra Teixeira, et al., "Prolonged cardioprotective effect of pyridostigmine encapsulated in liposomes," Life Sciences, vol. 86, 2010, pp. 17-23.
Wang, Timothy C., et al., "Pancreatic Gastrin Stimulates Islet Differentiation of Transforming Growth Factor a-Induced Ductular Precursor Cells," The Journal of Clinical Investigation, Inc., Sep. 1993, vol. 92, pp. 1349-1356.
Wang, Jingxiong, et al., "Phospholipid metabolite 1-palmitoyl-lysophosphatidylcholine enhances human ether-a-go-go-related gene (HERG) K+ channel function", Circulation, 2001, vol. 104, No. 22, pp. 2645-2648.
Wesley, Umadevi V., et al., "Role for Dipeptidyl Peptidase IV in Tumor Suppression of Human Non Small Cell Lung Carcinoma Cells," Int. J. Cancer, (2004), 109:855-866.
Wesley, Umadevi V., et al., "Dipeptidyl Peptidase Inhibits Maignant Phenotype of Prostate Cancer Cells by Blocking Basic Fibroblast Growth Factor Signaling Pathway," Cancer Res. (2005), a65:1325-1334.
Witchel, "Drug-induced hERG Block and Long QT Syndrome," Cardiovascular Therapeutics, 2011, vol. 29, pp. 251-259.
Wu, Aiguo, et al., "Brain and Spinal Cord Interaction: A Dietary Curcumin Derivative Counteracts Locomotor and Cognitive Deficits After Brain Trauma," Neurohabil Neural Repair, May 2011, 25(4):332-342.
Xalkori Package insert, Pfizer Laboratories, revised Feb. 2013, 10 pp.
Xu, Ying, et al., "Curcumin Reverses Impaired Hippocampal Neurogenesis and Increases Serotonin Receptor 1A mRNA and Brain-Derived Neurotrophic Factor Expression in Chronically Stressed Rats," Brain Research, (2007), 1162, pp. 9-18.
Yang, Ping, et al., "Allelic Variants in Long-QT Disease Genese in Patients with Drug Associated Rosades de Pointes," Circulation, Apr. 23, 2002, pp. 1943-1948.
Yap, Y. G., et al., "Drug Induced QT Prolongation and Torsades de Pointes," Heart, vol. 89, Nov. 2003, pp. 1363-1372.
Zachariae, U., et aL, "Side chain flexabilities in the human ether-a-go-go related potassium channel (hERG) together with matched-pair binding studies suggest a new binding mode for channel blockers," J. Med. Chem., vol. 52 (14),Jan. 2, 2009, pp. 4266-4276.
Zhang, L., et al., "Self-Assembled Lipid—Polymer Hybrid Nanoparticles: A Robust Drug Delivery Platform," ACS Nano, vol. 2:8, Jul. 23, 2008, pp. 1696-1702.
Zhou, L., et al., "Nilotinib for Imatinib-Resistant or -Intolerant Chronic Myeloid Leukemia in Chronic Phase, Accelerated Phase, or Blast Crisis: A Single- and Multiple-Dose, Open-Label Pharmacokinetic Study in Chinese Patients," Clinical Therapeutics, vol. 31:7, Jul. 2009, pp. 1568-1575.
Extended European Search Report and Europeean Search Opinion for EPO 10832224.9 dated Feb. 26, 2013, 5 pages.
Extended and Supplemental European Search Report for EPO 11760055.1 dated Jun. 13, 2014, 7 pages.
Extended European Search Report and Europeean Search Opinion for EPO 12757689.0 dated Oct. 22, 2014, 7 pages.
Extended European Search Report and European Search Opinion for 12792560.0 dated Oct. 30, 2014, 11 pages.
International Search Report and Written Opinion for PCT/US2010/057332, dated Aug. 2, 2011, 12 pages.
International Search Report and Written Opinion for PCT/US2011/029393, dated Jun. 23, 2011, 17 pages.
International Search Report and Written Opinion for PCT/US2012/029230, dated Sep. 21, 2012, 14 pages.
International Search Report and Written Opinion for PCT/US2012/040637, dated Dec. 12, 2012, 13 pages.
International Search Report and Written Opinion for PCT/US2014/071246, dated Mar. 27, 2015, 14 pages.
International Search Report and Written Opinion for PCT/US2015/034078, dated Aug. 31, 2015, 17 pages.
International Search Report and Written Opinion for PCT/US2013/057744 dated Dec. 12, 2013, 14 pages.

(56) References Cited

OTHER PUBLICATIONS

Abel, Ted., et al., "Epigenetic Targets of HDAC Inhibition in Neurodegenerative and Psychiatric Disorders," Current Opinion in Pharmacology, (2008), vol. 8, pp. 57-64.

Aggarwal, et al., "The Molecular Targets and Therapeutic Uses of Curcumin in Health and Disease," (2006), Springer, 515 pages.

Anderson, P., et al., "The Hippocampus Book," Oxford University Press, 2006, 102 pages.

Anderson, Corey, et al., "Most LQT2 Mutations Reduce Kv11.1 (hERG) Current by a Class 2 (Trafficking-Deficient) Mechanism," Circuilation, Nov. 11, 2005, pp. 365-373.

Arbiser, Jack L., et al., "Curcumin is an In Vivo Inhibitor of Angiogenesis," Moledular Medicine, (1998), 4:376-383.

Ataie, Amin, et al., "Neuroprotective Effects of the Polyphenolic Antioxidant Agnet, Curcumin, Against Homocysteine-Induced Cognitive Impairment and Oxidative Stress in the Rat," Pharmacology, Biochemistry and Behavior, (2010), vol. 96, pp. 378-385.

Bala, Kiran, et al., "Neuroprotective and Anti-Aging Effects of Curcumin in Aged Rat Brain Regions," Biogerontology, (2006), vol. 7, pp. 81-89.

Begum, A.N., et al., "Curcumin Structure-Function, Bioavailibility, and Efficacy in Models of Neuroinflammation and Alzheimer's Disease," The Journal of Pharmacoloby and Experimental Therapeutics, vol. 326:1, Apr. 15, 2008, pp. 196-208.

Bentzen, Peter J., et al., "Curcumin Induced Suicidal Erythrocyte Death," Cellular Physiology and Biochemistry, (2007), 19:153-164.

Bisht, Savita, et al., "Polymeric Nanoparticle-Encapsulated Curcumin ("Nanocurcumin"): A Novel Strategy for Human Cancer Therapy," Journal of Nanobiotechnology, (2007), 18 pages.

Bisht, Savita, et al., "Systemic Administration of Polymeric Nanoparticle-Encapsulated Curcumin (NanoCurcTM) Blocks Tumor Growth and Metastases in Preclinical Models of Pancreatic Cancer," Mol. Cancer Ther., (Aug. 2010), 9(8):2255-2264.

Blomgren, Kerstin, et al., "Obesity and Treatment of Diabetes with Glyburide may Both be Risk Factors for Acute Pancreatitis," Diabetes Care, (2002), 25:298-302.

Brownlee, Michael, "Biochemistry and Molecular Cell Biology of Diabetic Complications," Nature, Dec. 13, 2001, vol. 414, pp. 813-820.

Chao, Chun C., et al., "Glia: The Not So Innocent Bystanders," Journal of NeuroVirology, (1996), 2:234-239.

Chen, Shali, et al., "High glucose-induced, endothelin-dependent fibronectin synthesis is mediated via NF-kB and AP-1," Am J. Physiol. Cell Physiol., Sep. 18, 2002, 284:C263-C272.

Chen, et al., "An in vitro study of liposomal curcumin: stability, toxicity and biological activity in human lymphocytes and epstein-barr virus-transformed human B-cells," International Journal of Pharmaceutics, Jan. 2009, vol. 366, Issue 1-2, pp. 133-139.

Chiu, Jane, et al., "Curcumin Prevents Diabetes-Associated Abnormalities in the Kidneys by Inhibiting p300 and Nuclear Factor-kB," Nutrition, (2009), 25:964-972.

Compton, SJ, et al., "Genetically Defined Therapy of Inherited Long-QT Syndrome. Correction of Abnormal Repolarization by Potassium," Circulation, 1996; 94:1018-1022.

Crack, Peter J., et al., "Glutathione Peroxidase-1 Contributes to the Neuroprotection Seen in the Superoxide Dismutase-1 Transgenic Mouse in Response to Ischemia/Reperfusion Injury," Journal of Cerebral Blood Flow and Metabolism, (2003), vol. 23, No. 1, pp. 19-22.

Crouch, et al., "Clinical Relevance and Management of Drug-Related QT Interval Prolongation," Pharmacotherapy, Nov. 7, 2003, vol. 23:7, pp. 881-908.

D'Amico, Michele, et al., "Long-Term Inhibition of Dipeptidyl Peptidase-4 in Alzheimer's Prone Mice," Experimental Gerontology 45,3, (2010), 24 pages.

Djeddi, D, et al., "A: Effect of Domperidone on QT Interval in Neonates," J Pediatrics, 2008; 153(5):596-598.

Doherty, K., et al., "Multi-parameter in vitro toxicity testing of crizotinib, sunitinib, erlotinib, and nilotinib in human cardiomyocytes," Toxicoloty and Applied Pharmacology, Apr. 28, 2003, vol. 272, pp. 245-255.

Ducroq, J, et al., "Printemps R, Le Grand M.: Additive Effects Ziprasidone and D,L-Sotalol on the Action Potential in Rabbit Purkinje Fibers and on the hERG Potassium Current," J.Pharmacol. Toxicol Methods, 2005; 52:115-122.

Rodrigues, C., et al., "Derivative Spectrophotmetry as a Tool for the Determination of Drug Partition Coefficients in water/dimyristoyl-L-α-phosphatidylglycerol (DMPG) Liposomes," Biophysical Chemistry (2001); 94:97-106.

Van Dijck, P.W.M., et al., "Influence of Ca2+ and Mg2+ on the thermotropic behaviour and permeability properties of liposomes prepared from dimyristoyl phosphatidylglycerol and mixtures of dimyristoyl phosphatidylglycerol and dimyristoyl phosphatidylcholine," Biochimica et Biophysica Acta (1975); 406:465-478.

Chartrand, et al., "Potential role of the membrane in hERG channel functioning and drug-induced long QT syndrome," Biochimica et Biophysica Acta, May 25, 2010, vol. 1798, pp. 1651-1662.

Chayanupatkul, "Cirrhotic cardiomyopathy: review of pathophysiology and treatment." Hepatol Int., Jul. 2014, vol. 8, No. 3, pp. 308-315.

Dhandapani, K. M., et al., "Curcumin suppresses growth and chemoresistance of human glioblastoma cells via AP-1 and NFkB transcription factors," J. Neurochem (2007) 102:522-538.

Dhule, S.S., et al., "The Combined Effect of Encapsulating Curcumin and C6 Ceramide in Liposomal Nanoparticles against Osteosarcoma," Molecular Pharmaceutics, vol. 11, No. 2, Dec. 31, 2013, pp. 417-427.

Extended European Search Report and European Search Opinion for 14864686.2 dated May 4, 2017, 8 pages.

Extended European Search Report and European Search Opinion for 16188460.6 dated Nov. 16, 2016, 12 pages.

Gilenya (Fingolimod) Full Prescribing Information, Novartis: T2016-22, Feb. 2016, 25 pp.

Gou, M., et al., "Curcumin-loaded biodegradable polymeric micelles for colon cancer therapy in vitro and in vivo," Nanoscale, vol. 3, No. 4, Oct. 2010, pp. 1558-1567.

International Search Report and Written Opinion for PCT/US2013/045898, dated Sep. 6, 2013, 12 pages.

Leung, et al., "Effective stablization of curcumin by association to plasma proteins: human serum albumin and fibronogen," Langmuir, Mar. 25, 2009, vol. 25, Issue 10, pp. 5773-5777.

National Biodiversity Authority, Secretary of Government of India, Third Party Observation for Application No. EP20110760055, submitted for observation on Jul. 20, 2017, 7 pp.

Pisarik, et al., "Reduction of free amphothericin B Acute Toxicity in Mice after intravenous administration of empty liposomes," Journal of Infectious Diseases, May 1990, 161(5), pp. 1042-1044.

Ramachandran, C., et al., "Potentiation of Etoposide and Temozolomide Cytotoxicity by Curcumin and Turmeric Force in Brain Tumer Cell Lines," Journal of Complementary and Integrative Medicine (2012), 9(1):Article 20.

Ranjan, A.P., et al., "Efficacy of Liposomal Curcumin in a Human Pancreatic Tumor Xenograft Model: Inhibition of Tumor Growth and Angiogensis," Anticancer Research, vol. 33, No. 9, Jul. 26, 2013, pp. 3603-3609.

Ravindran, J., et al., "Curcumin and Cancer Cells: How Many Ways Can Currly Kill Tumor Cells Selectively?," The AAPS Journal, vol. 11:3, Sep. 2009, pp. 495-510.

Tang, H., et al., "Curcumin Polymers as Anticancer Conjugates," Biomaterials, vol. 31, No. 27, Jun. 29, 2010, pp. 7139-7149.

Tudor, B-A, et al., "Amphotericin B® treatment causes QT prolongation in lung transplant-pateints," Intensive Care Medicine Experimental, Oct. 2015, 3(Suppl 1):A213 poster presentation.

WHO Model List of Essential Medicines, World Health Organization, Oct. 2013. pp. 1-47.

Wong-Beringer, Annie, et al., "Lipid Formulations of Amphotericin B: Clinical Efficacy and Toxicities," Clinical Infectious Diseases, May 4, 1998, vol. 27, pp. 603-618.

Yagi, Y., et al., "Analysis of Onset Mechanisms of a Sphingosine 1-Phosphate Receptor Modulator Fingolimod-Induced Atrioven-

(56) References Cited

OTHER PUBLICATIONS tricular Conduction Block and QT-Interval Prolongation," Toxicology and Applied Pharmacology, Sep. 16, 2014, 281, pp. 39-47.
Zeltser, et al., "Drug-induced atrioventricular block: prognosis after discontinuation of the culprit drug." Journal of the American College of Cardiology, Jul. 2004, vol. 44, No. 1, pp. 105-108.
International Search Report and Written Opinion for PCT/US2017/057446, dated Dec. 29, 2017, 13 pp.
Shopp, G.M., et al., "Liposomes ameliorate Crizotinib- and Nilotinib-induced inhibition of the cardiac IKr channel and Qtc prolongation," Anticancer Research, 2014, vol. 34, pp. 4733-4740.
International Search Report and Written Opinion of Korean Intellectual Property Office for PCT/US2017/060936 dated Feb. 20, 2018, 13 pp.

* cited by examiner

PROTECTIVE EFFECT OF DMPC, DMPG, DMPC/DMPG, LYSOPG AND LYSOPC AGAINST DRUGS THAT CAUSE CHANNELOPATHIES

CROSS-REFERENCE TO RELATED APPLICATIONS

This application is a continuation-in-part patent application of U.S. patent application Ser. No. 15/068,300 filed on Mar. 11, 2016, which is a continuation application that claims priority to U.S. patent application Ser. No. 14/268,376 filed on May 2, 2014, which is a continuation application that claims priority to U.S. patent application Ser. No. 13/487,233 filed on Jun. 3, 2012, now U.S. Pat. No. 8,753,674 issued on Jun. 17, 2014, which claims priority to U.S. Provisional Application Ser. No. 61/493,257 filed Jun. 3, 2011; this application is also a continuation-in-part patent application of U.S. patent application Ser. No. 14/575,644, filed on Dec. 18, 2014, which claims priority to U.S. Provisional Application Ser. No. 61/917,426 filed on Dec. 18, 2013, and U.S. Provisional Application Ser. No. 61/977,417 filed on Apr. 9, 2014; this application is also a continuation-in-part patent application of U.S. patent application Ser. No. 14/729,940 filed on Jun. 3, 2015, which claims priority to U.S. Provisional Application Ser. No. 62/007,244 filed on Jun. 3, 2014, U.S. Provisional Application Ser. No. 62/035,417 filed Aug. 9, 2014, U.S. Provisional Application Ser. No. 62/056,957 filed Sep. 29, 2014, U.S. Provisional Application Ser. No. 62/150,059 filed Apr. 20, 2015, the entire contents of which are incorporated herein by reference.

STATEMENT OF FEDERALLY FUNDED RESEARCH

None.

INCORPORATION-BY-REFERENCE OF MATERIALS FILED ON COMPACT DISC

None.

TECHNICAL FIELD OF THE INVENTION

The present invention relates in general to the field of drug treatment, and more particularly, to novel compositions and methods for reducing or eliminating channelopathies or conditions resulting from irregularities or alterations in cardiac patterns caused by an active agent or a drug.

BACKGROUND OF THE INVENTION

Without limiting the scope of the invention, its background is described in connection with compositions and methods for controlling the duration of repolarization of the cardiac ventricle QT in a subject comprising administering to subject in need thereof of a modification of or functional interference with a therapeutic agent, or congenital defect which if unmodified can induce prolongation of repolarization in the heart myocyte action potential, torsade de points, and the long QT syndrome.

The beating of the heart is due to precisely controlled regularly spaced waves of myocardial excitation and contraction. The electrical currents during ion-based depolarization and repolarization can be measured by electrical leads placed on the body in specific locations (the electrocardiogram) which measure electrical waves. The P-wave represents a wave of depolarization in the atrium. When the entire atria becomes depolarized, the wave returns to zero. After 0.1 seconds the ventricle is entirely depolarized resulting in the QRS complex. The three peaks are due to the way the current spreads in the ventricles. This is followed by the T-wave or repolarization of the ventricle. The QT interval measured from the beginning of the QRS complex to the end of the T wave on the standard ECG represents the duration till the completion of the repolarization phase of the cardiac myocyte (or the depolarization and repolarization of the ventricle). The duration of this interval can vary due to genetic variation, cardiac disease, electrolyte balance, envenomation, and drugs. Prolongation of the QT interval can result in ventricular arrhythmias and sudden death.

Drug induced long QTc Syndrome (LQTS) i.e., a prolongation of the action potential duration is a common cause of governmental mandated drug withdrawal. QTc prolongation is an unpredictable risk factor for Torsades de Pointes (TdP), a polymorphic ventricular tachycardia leading to ventricular fibrillation. Drug induced LQTS comprises about 3% of all prescriptions which when followed by TdP may constitute a lethal adverse reaction. Patients taking one or more than one QTc-prolonging drug concomitantly, have an enhanced risk of TdP. While the overall occurrence of TdP is statistically rare but clinically significant for the affected individual, assay for this drug effect is a mandatory requirement prior to allowing a drug to enter clinical trials.

Common structurally diverse drugs block the human ether-a-go-go-related gene (KCNH2 or hERG) coded $K^+$ channel and the cardiac delayed-rectifier potassium current $I_K$ (KV11.1) resulting in acquired LQTS. Drug-associated increased risk of LQTS is a major drug development hurdle and many drugs have been withdrawn during pre-clinical development, or assigned black box warnings following approval or withdrawn from the market. Autosomal recessive or dominant LQTS based upon 500 possible mutations in 10 different genes coding for the potassium channel has an incidence of 1:3000 or about 100,000 persons in the US. Prolonged QT intervals, or risk of LQTS occur in 2.5% of the asymptomatic US population. This syndrome when expressed can lead to severe cardiac arrhythmia and sudden death in untreated patients. The probability of cardiac death in patients with asymptomatic congenital LQTS who are medicated with LQTS-inducing drugs is increased.

The majority of the acquired LTQS drug withdrawals are due to obstruction of the potassium ion channels coded by the human ether-a-go-go related gene (hERG). High concentrations of hERG blocking drugs generally induce a prolonged QTc interval and increase the probability of TdP. Up to 10% of cases of drug-induced TdP can be due to due to 13 major genetic mutations, 471 different mutations, and 124 polymorphisms (Chig, C 2006).

Systems and methods for detection of LQTS have been described previously. For example U.S. Patent Publication No. 2010/0004549 (Kohls et al. 2010) discloses a system and method of detecting LQTS in a patient by comparing a collected set of ECG data from the patient to a plurality of databases of collected ECG data. The plurality of databases will include a database containing previous ECGs from the patient, a known acquired LQTS characteristics database, and a known genetic LQTS characteristics database. Comparing the patient's ECG to these databases will facilitate the detection of such occurrences as changes in QT interval from success of ECGs, changes in T-wave morphology, changes in U-wave morphology, and can match known genetic patterns of LQTS. The system and method is sensitive to patient gender and ethnicity, as these factors have been shown to effect LQTS, and is furthermore capable of matching a QT duration to a database of drug effects. The system and method is also easily integrated into current ECG management systems and storage devices.

A system and method for the diagnosis and treatment of LQTS is described in U.S. Patent Publication No. 2008/0255464 (Michael, 2008). The Michael invention includes a system for diagnosing Long QT Syndrome (LQTS) derives a QT/QS2 ratio from an electrical systole (QT) and a mechanical systole (QS2) to detect a prolonged QT interval in a patient's cardiac cycle. A processor acquires the systoles from a microphone and chest electrodes, calculates the QT/QS2 ratio, and outputs the result to a display. The processor may compare the QT/QS2 ratio to a threshold value stored in memory for diagnosing LQTS in the patient. A user interface provides for programming, set-up, and customizing the display. A mode selector allows the system to operate alternatively as a phonocardiograph, a 12 lead electrocardiograph, or a machine for diagnosing LQTS. A related method for diagnosing cardiac disorders such as LQTS includes measuring QT and QS2 during a same cardiac cycle, calculating a QT/QS2 ratio, and comparing the result to a threshold value derived from empirical data. The method may include measuring systoles both at rest and during exercise, and may be used for drug efficacy, dosage optimization, and acquired LQTS causality tests.

A method for the treatment of cardiac arrhythmias is provided in U.S. Patent Publication No. 2007/0048284 (Donahue and Marban, 2007). The method includes administering an amount of at least one polynucleotide that modulates an electrical property of the heart. The polynucleotides of the invention may also be used with a microdelivery vehicle such as cationic liposomes and adenoviral vectors.

Methods, compositions, dosing regimes, and routes of administration for the treatment or prevention of arrhythmias have been described by Fedida et al. (2010) in U.S. Patent Publication No. 2001/00120890. In the Fedida invention, early after depolarizations and prolongation of QT interval may be reduced or eliminated by administering ion channel modulating compounds to a subject in need thereof. The ion channel modulating compounds may be cycloalkylamine ether compounds, particularly cyclohexylamine ether compounds. Also described are compositions of ion channel modulating compounds and drugs which induce early after depolarizations, prolongation of QT interval and/or Torsades de Pointes. The Fedida invention also discloses antioxidants which may be provided in combination with the ion channel modulating compounds, non-limiting examples of the antioxidants include vitamin C, vitamin E, beta-carotene, lutein, lycopene, vitamin B2, coenzyme Q10, cysteine as well as herbs, such as bilberry, turmeric (curcumin), grape seed or pine bark extracts, and ginkgo.

SUMMARY OF THE INVENTION

In one embodiment, the present invention includes a composition comprising: one or more pharmacologically active agents that induce a cardiac channelopathy or a condition resulting from the irregularity or alteration in the cardiac pattern in a subject and one or more lipids provided in an amount sufficient to prevent or reduce the cardiac channelopathy or the condition resulting from the irregularity or alteration in the cardiac pattern caused by the one or more pharmacologically active agents, wherein the combination is dispersed in a pharmaceutically acceptable medium, solvent, or vehicle, wherein the active agent, the lipids, or both are dissolved, dispersed, or suspended in the medium, the solvent, or the vehicle. In one aspect, the one or more pharmacologically active agents is/are selected from at least one of 5-HT3 antagonists that block serotonin binding, 5-HT4 receptor agonists, histamine antagonists, calcium channel blockers, anti-malarial agents, antipsychotic agents, halodols, antibiotics, anti-arrhythmics, anti-cancer agents, opioids, or hypolipidemic agents. In another aspect, the lipid comprises at least one of a phosphatidylcholine, a phosphatidylethanolamine, a phosphatidylserine, a phosphatidylglycrol, a cardiolipin, a phosphatidylinositol or a precursor thereof. In another aspect, the lipid comprises a lysophosphatidylglycerol, a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine, erucoyl-lysophosphatidylcholine, 1-Myristoyl-2-Hydroxy-sn-Glycero-3-Phosphocholine (DMPC), 12-Mysteroyl-2-Hydroxy-sn-Glycero-3-[Phospho-rac-(glycerol)] (DMPG), DMPC/DMPG, 1-myristoyl-2-hydroxy-sn-glycero-3-phospho-(1'-rac-glycerol) (LysoPG), or 1-myristoyl-2-hydroxy-sn-glycero-3-phosphocholine (LysoPC). In another aspect, the lipid is a lysophosphatidylglycerol defined further as a short chain fatty acid is up to 5 carbons, a medium chain is 6 to 12 carbons, a long chain is 13-21 carbons and a very long chain fatty acid is greater than 22 carbons, including both even and odd chain fatty acids. In another aspect, the lipid comprises a short chain fatty acid that has 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated. In another aspect, the cardiac channelopathy or the condition resulting from the irregularity or alteration in the cardiac pattern is inhibition of an ion channel responsible for the delayed-rectifier $K^+$ current in the heart, polymorphic ventricular tachycardia, prolongation of the QTc, LQT2, LQTS, or torsades de pointes. In another aspect, the active agent drug is selected from at least one of crizotinib, nilotinib, terfenadine, astemizole, gripafloxacin, terodilene, droperidole, lidoflazine, levomethadyl, sertindoyle or cisapride. In another aspect, the composition is adapted for enteral, parenteral, intravenous, intraperitoneal, cutaneous, subcutaneous, pulmonary, rectal, vaginal, or oral administration.

In another aspect, the active agent is provided in a lipid that is formed into a liposome, wherein the lipid is selected from at least one of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, or diacylglycerolsuccinate. In another aspect, the active agent is selected from Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Curcumin, Crizotinib, Dabrafenib, Dasatinib, Desipramine, Dexmedetomidine, Dexmethylphenidate, Dextroamphetamine, d-Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

In another embodiment, the present invention includes a method for preventing or treating one or more a cardiac channelopathy or a condition resulting from the irregularity or alteration in the cardiac pattern, in a human or animal subject caused by a pharmacologically active agent used to treat a disease, comprising the steps of: preparing a composition comprising a lipid adapted for administration effective to reduce or prevent the cardiac channelopathy or condition resulting from the irregularity or alteration in the cardiac pattern with the active agent, wherein the amount of the lipid is sufficient to reduce or eliminate the cardiac channelopathy or condition resulting from the irregularity or alteration in the cardiac pattern caused by the active agent; and administering to the human or animal subject the composition in an amount sufficient to treat the disease. In one aspect, the one or more pharmacologically active agents is/are selected from at least one of 5-HT3 antagonists that block serotonin binding, 5-HT4 receptor agonists, histamine antagonists, calcium channel blockers, anti-malarial agents, antipsychotic agents, halodols, antibiotics, anti-arrhythmics, anti-cancer agents, opioids, or hypolipidemic agents. In another aspect, the lipid comprises at least one of a phosphatidylcholine, a phosphatidylethanolamine, a phosphatidylserine, a phosphatidylglycrol, a cardiolipin, a phosphatidylinositol or a precursor thereof. In another aspect, the lipid comprises at least one of a lysophosphatidylglycerol, a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine, erucoyl-lysophosphatidylcholine, 1-Myristoyl-2-Hydroxy-sn-Glycero-3-Phosphocholine (DMPC), 12-Mysteroyl-2-Hydroxy-sn-Glycero-3-[Phospho-rac-(glycerol)] (DMPG), DMPC/DMPG, 1-myristoyl-2-hydroxy-sn-glycero-3-phospho-(1'-rac-glycerol) (LysoPG), or 1-myristoyl-2-hydroxy-sn-glycero-3-phosphocholine (LysoPC). In another aspect, the lipid is a lysophosphatidylglycerol defined further as a short chain fatty acid is up to 5 carbons, a medium chain is 6 to 12 carbons, a long chain is 13-21 carbons and a very long chain fatty acid is greater than 22 carbons, including both even and odd chain fatty acids. In another aspect, the lipid comprises a short chain fatty acid that has 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated. In another aspect, the cardiac channelopathy or the condition resulting from the irregularity or alteration in the cardiac pattern is inhibition of an ion channel responsible for the delayed-rectifier $K^+$ current in the heart, polymorphic ventricular tachycardia, prolongation of the QTc, LQT2, LQTS, or torsades de pointes. In another aspect, the one or more active agents is selected from at least one of crizotinib, nilotinib, terfenadine, astemizole, gripafloxacin, terodilene, droperidole, lidoflazine, levomethadyl, sertindoyle or cisapride. In another aspect, the method further comprises adapting the composition for enteral, parenteral, intravenous, intraperitoneal, cutaneous, subcutaneous, pulmonary, rectal, vaginal, or oral administration. In another aspect, the active agent is selected from Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Curcumin, Crizotinib, Dabrafenib, Dasatinib, Desipramine, Dexmedetomidine, Dexmethylphenidate, Dextroamphetamine, d-Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

Another embodiment of the present invention includes a method for preventing or treating a cardiac channelopathy or condition resulting from the irregularity or alteration in the cardiac pattern caused by an active agent in a human or animal subject comprising the steps of: identifying the subject in need of treatment for a disease treatable with the active agent that causes the cardiac channelopathy; and providing a composition comprising a lipid in an amount effective to reduce or prevent the cardiac channelopathy or condition resulting from the irregularity or alteration in the cardiac pattern with an effective amount of the active agent sufficient to treat the disease. In one aspect, the active agent has previously failed a clinical trial due to the cardiac channelopathy or condition resulting from the irregularity or alteration in the cardiac pattern. In another aspect, the method further comprises the step of identifying a drug in a clinical trial that failed or has limited clinical use due to the cardiac channelopathy or condition resulting from the irregularity or alteration in the cardiac pattern caused by the drug, and reformulating the drug with the lipid to reduce or eliminate the cardiac channelopathy or condition resulting from the irregularity or alteration in the cardiac pattern caused by the drug. In another aspect, the active agent is selected from Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Curcumin, Crizotinib, Dabrafenib, Dasatinib, Desipramine, Dexmedetomidine, Dexmethylphenidate, Dextroamphetamine, d-Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

Yet another embodiment of the present invention includes a method of evaluating a candidate drug for the treatment of a disease or condition, wherein the candidate drug causes a cardiac channelopathy or condition resulting from the irregularity or alteration in the cardiac pattern caused by the candidate agent, the method comprising: (a) administering an amount of a lipid, a liposome, or a lipid precursor and the candidate drug to a first subset of the patients, and a placebo to a second subset of the patients, wherein the lipid, liposome, or lipid precursor is provided in an amount effective to reduce or prevent one or more cardiac channelopathies or conditions resulting from irregularities or alterations in cardiac patterns caused by the candidate drug; (b) measuring the level of cardiac channelopathy or condition resulting from the irregularity or alteration in the cardiac pattern from the first and second set of patients; and (c) determining if the combination of the lipid, liposome, or lipid precursor and the candidate drug reduce the channelopathy or condition resulting from the irregularity or alteration in the cardiac pattern that is statistically significant as compared to any reduction occurring in the subset of patients that took the placebo or to the known cardiac channelopathy or condition resulting from the irregularity or alteration in the cardiac pattern, wherein a statistically significant reduction indicates that the combination of the lipid, liposome, or lipid precursor and the candidate drug is useful in treating the disease state or condition while also reducing or eliminating the drug-induced cardiac channelopathy or condition resulting from the irregularity or alteration in the cardiac pattern. In one aspect, the drug has previously failed a clinical trial due to the cardiac channelopathy or condition resulting from the irregularity or alteration in the cardiac pattern. In another aspect, the drug has been withdrawn from the marketplace due to the cardiac channelopathy or condition resulting from the irregularity or alteration in the cardiac pattern. In another aspect, the method further comprises the step of repeating steps (a) to (c) after a period of time. In another aspect, the active agent is selected from Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Curcumin, Crizotinib, Dabrafenib, Dasatinib, Desipramine, Dexmedetomidine, Dexmethylphenidate, Dextroamphetamine, d-Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
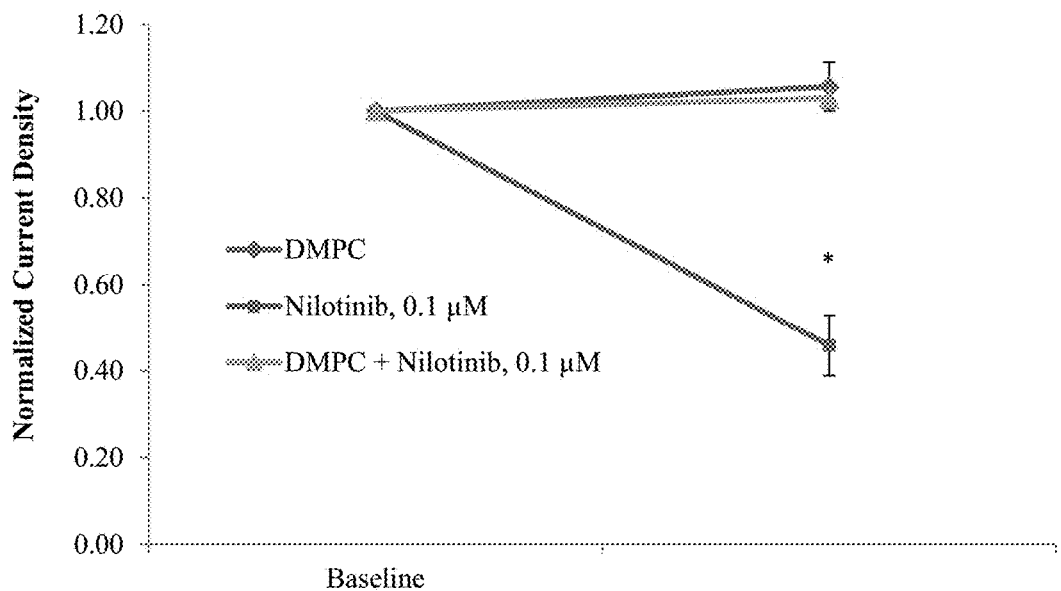
FIG. 1 is a graph that shows the effect of DMPC, DMPC+Nilotinib and Nilotinib on hERG current density from transfected HEK 293 cells.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Non-limiting exemplary lipids for use with the present invention include, e.g., phosphatidylcholine, a phosphatidylethanolamine, a phosphatidylserine, a phosphatidylglycrol, a cardiolipin, a phosphatidylinositol or a precursor thereof in lipid, liposome, or lyso form. Non-limiting examples of lipids include lysophosphatidylglycerols for use with the present invention include lysophosphatidylcholines, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine or erucoyl-lysophosphatidylcholine. Asymmetric phosphatidylcholines are referred to as 1-acyl, 2-acyl-sn-glycero-3-phosphocholines, wherein the acyl groups are different from each other. Symmetric phosphatidylcholines are referred to as 1,2-diacyl-sn-glycero-3-phosphocholines. As used herein, the abbreviation "PC" refers to phosphatidylcholine. The phosphatidylcholine 1,2-dimyristoyl-sn-glycero-3-phosphocholine is abbreviated herein as "DMPC." The phosphatidylcholine 1,2-dioleoyl-sn-glycero-3-phosphocholine is abbreviated herein as "DOPC." The phosphatidylcholine 1,2-dipalmitoyl-sn-glycero-3-phosphocholine is abbreviated herein as "DPPC." The single fatty acid chain version of these short or long chain fatty acids are referred to as the "lyso" forms when only a single fatty acid chain is attached to the glyceryl backbone.

In one embodiment, the lysophosphatidylglycerol has a basic structure:

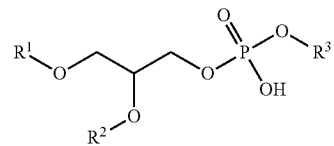

wherein $R^1$ or $R^2$ can be any even or odd-chain fatty acid, and $R^3$ can be H, acyl, alkyl, aryl, amino acid, alkenes, alkynes, and wherein a short chain fatty acid is up to 5 carbons, a medium chain is 6 to 12 carbons, a long chain is 13-21 carbons and a very long chain fatty acid is greater than 22 carbons, including both even and odd chain fatty acids. In one example, the fatty acids have 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or long fatty acids, which can be saturated or unsaturated.

The present invention can be used with any QT prolonging drug, including but not limited to those listed at: www.crediblemeds.org, including: Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin and piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

The single most common cause of the withdrawal or restriction of the use of marketed drugs has been QT-interval prolongation associated with polymorphic ventricular tachycardia, or torsade de pointes, a condition that can be fatal.

5-HT3 Antagonists Blocks Serotonin Binding.

Aloxi (or palonasitron HCL) is an antiemetic for chemotherapy induced nausea and vomiting, a 5-HT 3 antagonist, blocks serotonin binding to 5-HT3. In a study there was no significant difference in the QTc intervals during the perioperative period, whether 0.075 mg of palonosetron is administered before or after sevoflurane anaesthesia. Palonosetron may be safe in terms of QTc intervals during sevoflurane anaesthesia.

5-HT4 Receptor Agonist.

Cisapride is a gastroprokinetic agent, a drug that increases motility in the upper gastrointestinal tract. It acts directly as a serotonin 5-HT4 receptor agonist and indirectly as a parasympathomimetic. Cisapride dose-dependently prolongs the QT interval. Neither torsade de pointe nor ventricular tachycardia were noted when monitoring 33 patients during a higher dose stage.

Histamine Antagonist.

Antihistamines used in the treatment of allergy act by competing with histamine for H1-receptor sites on effector cells. They thereby prevent, but do not reverse, responses mediated by histamine alone.

Pain and Premenstrual Symptom Relief H1 antagonists are most useful in acute exudative types of allergy that present with symptoms of rhinitis, urticaria, and conjunctivitis. Their effect, however, is purely palliative and confined to the suppression of symptoms attributable to the histamine-antibody reaction Pyrilamine is a diuretic first-generation histamine H1 antagonist. There is a case of an adolescent with prolonged QT interval after an overdose of pyrilamine. Reports of deaths resulting from ventricular tachyarrhythmias have been made.

Terfenidine is an antihistamine, used to treat allergies, hives (urticaria), and other allergic inflammatory conditions. The brand name Seldane is discontinued in the U.S. Rare reports of severe cardiovascular adverse effects have been received which include ventricular tachyarrhythmias (torsades de pointes, ventricular tachycardia, ventricular fibrillation, and cardiac arrest), hypotension, palpitations, syncope Loratidine is a first-line antihistamine is a second-generation peripheral histamine H1-receptor blocker. In structure, it is closely related to tricyclic antidepressants, such as imipramine, and is distantly related to the atypical antipsychotic quetiapine. Some antihistamines, such as mizolastine and ebastine, can prolong the QT interval and provoke severe cardiac arrhythmias. As of mid 2009 very few clinical data had been published on the risk of QT prolongation with loratadine. Very rare reported cases of torsades de pointes linked to loratadine mainly appear to involve drug interactions, especially with amiodarone and enzyme inhibitors. There are no reports of QT prolongation attributed to desloratadine, the main metabolite of loratadine. Patients who have risk factors for torsades de pointes or who are taking certain enzyme inhibitors should avoid using loratadine. I Astemizole is a long-acting and highly selective H1 antagonist, acting on histamine H-1 receptor and H-3 receptors. It has antipruritic, and anticholinergic effects. It is also a functional inhibitor of acid sphingomyelinase. An overdose of astemizole predisposes the myocardium to ventricular dysrhythmias, including torsades de pointes. However, dysrhythmias developed only in patients with corrected QT intervals greater than 500 ms.

Calcium Channel Blockade.

Prenylamine is a calcium channel blocker of the amphetamine chemical class that is used as a vasodilator in the treatment of angina pectoris. Resting ECGs were recorded in 29 patients with angina pectoris before, during and after treatment with prenylamine 180 mg daily. The QT interval became significantly prolonged after one week of treatment. The prolongation persisted as long as therapy was continued, which was up to 6 months. After withdrawal of treatment the QT interval returned to normal within 2 weeks.

Lidoflazine is a piperazine calcium channel blocker is a coronary vasodilator with some antiarrhythmic action. As a tricyclic antihistamine, It acts as a selective inverse agonist of peripheral histamine H1-receptors. It carries a significant risk of QT interval prolongation and ventricular arrhythmia. Lidoflazine inhibits potently HERG current (I(HERG)) recorded from HEK 293 cells stably expressing wild-type HERG (IC(50) of approximately 16 nM). It is approximately 13-fold more potent against HERG than verapamil under similar conditions in preferentially inhibiting activated/open HERG channels. Lidoflazine produces high affinity blockade of the alpha subunit of the HERG channel by binding to aromatic amino acid residues within the channel pore and, second, that this is likely to represent the molecular mechanism of QT interval prolongation by this drug.

Bepridil is an antihypertensive drug which disrupts the movement of calcium (Ca2+) through calcium channels. While it prolongs the QT interval. Bepridil prolongs the QT and refractoriness and a linear correlation could be demonstrated between the percent change in QTc and refractory period prolongation. Bepridil in one patient reduced by one the number of stimuli required to induce VT, but no spontaneous arrhythmias were noted, It possesses antiarrhythmic properties with a minimal proarrhythmic effect.

Antimalarial.

Chloroquine-Chlorpheniramine, antimalarial, a chloroquine and chloroquine plus chlorpheniramine, a histamine H1 receptor blocker that reverses chloroquine insensitivity in *Plasmodium falciparum* in vitro, Chloroquine/chlorpheniramine produces a higher cure rate than chloroquine alone. Short QT Syndrome (SQTS) is a sporadic or autosomal dominant disorder characterized by markedly accelerated cardiac repolarization, ventricular arrhythmias and sudden cardiac death. To date, mutations in 5 different ion channel genes (KCNH2, KCNQ1, KCNJ2, CACNA1C and CACNB2) have been identified to cause SQTS. The risk of ventricular arrhythmias and sudden death is remarkably high in SQTS with cardiac arrest reported as a presenting symptom in 31% of SQTS subjects. Chloroquine Blocks a Mutant Kir2.1 Channel Responsible for Short QT Syndrome and Normalizes Repolarization Properties in silico.

Halofantrine is an antimalarial agent with a substituted phenanthrene, and is related to the antimalarial drugs quinine and lumefantrine. It can be associated with cardiotoxicity. The most dangerous side effect is cardiac arrhythmias: halofantrine causes significant QT prolongation, and this effect is seen even at standard doses. The drug should therefore not be given to patients with cardiac conduction defects and should not be combined with mefloquine. The mechanism of action of halofantrine is unknown.

Quinidine is an antimalarial acts as a class I antiarrhythmic agent (Ia) in the heart. It is a stereoisomer of quinine, This alkaloid dampens the excitability of cardiac and skeletal muscles by blocking sodium and potassium currents across cellular membranes. It prolongs cellular action potential, and decreases automaticity. Quinidine also blocks muscarinic and alpha-adrenergic neurotransmission. Quinidine causes greater QT prolongation in women than in men at equivalent serum concentrations. This difference may contribute to the greater incidence of drug-induced torsades de pointes observed in women taking quinidine and has implications for other cardiac and noncardiac drugs that prolong the QTc interval.

Antipsychotics.

First-generation antipsychotics, known as typical antipsychotics, were discovered in the 1950s. Most second-generation drugs, known as atypical antipsychotics, have been developed more recently, although the first atypical antipsychotic, clozapine, was discovered in the 1960s and introduced clinically in the 1970s. Both generations of medication tend to block receptors in the brain's dopamine pathways, but atypicals tend to act on serotonin receptors as well. Both generations of medication tend to block receptors in the brain's dopamine pathways, but atypicals tend to act on serotonin receptors as well. QTc interval prolongation can occur as a result of treatment with both conventional and novel antipsychotic medications and is of clinical concern because of its association with the potentially fatal ventricular arrhythmia, torsade de pointes.

Pimozide is an antipsychotic drug of the diphenylbutylpiperidine class, Can induce prolongation of the QT interval. Pimozide is contraindicated in individuals with either acquired, congenital or a family history of QT interval prolongation. Its use is advised against in individuals with people with either a personal or a family history of arrhythmias or torsades de pointes acts as an antagonist of the D2, D3, and D4 receptors and the 5-HT7 receptor. It is also a hERG blocker.

Sertindole is an antipsychotic medication. Like other atypical antipsychotics, it has activity at dopamine and serotonin receptors in the brain. Abbott Labs first applied for U.S. Food and Drug Administration (FDA) approval for sertindole in 1996, but withdrew this application in 1998 following concerns over the increased risk of sudden death from QTc prolongation. In a trial of 2000 patients on taking sertindole, 27 patients died unexpectedly, including 13 sudden deaths. The drug has not been approved by the FDA for use in the USA. In Europe, Sertindole was approved and marketed in 19 countries from 1996, but its marketing authorization was suspended by the European Medicines Agency in 1998 and the drug was withdrawn from the market. In 2002, based on new data, the EMA's CHMP suggested that Sertindole could be reintroduced for restricted use in clinical trials, with strong safeguards including extensive contraindications and warnings for patients at risk of cardiac dysrhythmias, a recommended reduction in maximum dose from 24 mg to 20 mg in all but exceptional cases, and extensive ECG monitoring requirement before and during treatment Chlorpromazine, marketed as Thorazine and Largactil, is an antipsychotic medication in the typical antipsychotic class. Its mechanism of action is not entirely clear but believed to be related to its ability as a dopamine antagonist. It also has anti-serotonergic and anti-histaminergic properties. Chlorpromazine is a very effective antagonist of D2 dopamine receptors and similar receptors, such as D3 and D5. Unlike most other drugs of this genre, it also has a high affinity for D1 receptors. Electrocardiogram QT corrected interval prolonged is reported only by a few people who take Thorazine. In a study of 2,633 people who have side effects while taking Thorazine from FDA and social media, 5 have electrocardiogram QT corrected interval prolonged.

Thioridazine is a piperidine typical antipsychotic drug belonging to the phenothiazine drug branded product was withdrawn worldwide in 2005 because it caused severe cardiac arrhythmias, however, generic versions are available in the US. The drug was voluntarily discontinued by its manufacturer, Novartis, worldwide because it caused severe cardiac arrhythmias. Thioridazine prolongs the QTc interval in a dose-dependent manner. The ratio of 5-HT2A to D2 receptor binding is believed to dictate whether or not most antipsychotics are atypical or typical. In thioridazine's case its ratio of 5-HT2A to D2 receptor binding is below the level that's believed to be required for atypicality despite its relatively low extrapyramidal side effect liability in practice.

Haldol, Haloperidol.

A typical antipsychotic medication QT interval prolongation is meperidine. It is on the WHO Model List of Essential Medicines, It is the most commonly used typical antipsychotic, Special cautions: patients at special risk for the development of QT prolongation (hypokalemia, concomitant use of other drugs causing QT Amiodarone: Q-Tc interval prolongation (potentially dangerous change in heart rhythm prolongation).

Mesoridazone is a piperidine neuroleptic drug belonging to the class of drugs called phenothiazines, used in the treatment of schizophrenia. It is a metabolite of thioridazine. Mesoridazine was withdrawn from the United States market in 2004 due to dangerous side effects, namely irregular heart beat and QT-prolongation of the electrocardiogram.

Selective Serotonin Reuptake Inhibitors.

Celaxa (citalopram) is an antidepressant in a group of drugs called selective serotonin reuptake inhibitors (SSRIs). Its chemical structure a racemic bicyclic phthalane derivative designated (±)-1-(3-dimethylaminopropyl)-1-(4-fluorophenyl)-1,3-dihydroisobenzofuran-5-carbonitrile, is unrelated to that of other SSRIs, or other available antidepressant agents.

Citalopram may cause a condition that affects the heart rhythm (QT prolongation). QT prolongation.

Antibiotics.

Moxifloxacin is a fourth-generation synthetic fluoroquinolone antibacterial agent. It functions by inhibiting DNA gyrase, a type II topoisomerase, and topoisomerase IV (enzymes necessary to separate bacterial DNA thereby inhibiting cell replication) may cause torsade de pointes. Coadministration of moxifloxacin with other drugs that also prolong the QT interval or induce bradycardia (e.g., beta-blockers, amiodarone) should be avoided. Careful consideration should be given in the use of moxifloxacin in patients with cardiovascular disease, including those with conduction abnormalities. Drugs that prolong the QT interval may have an additive effect on QT prolongation and lead to increased risk of ventricular arrhythmias.

Pentamidine is an antimicrobial medication given to prevent and treat *pneumocystis* pneumonia. The exact mechanism of its anti-protozoal action is unknown (though it may involve reactions with ubiquitin and mitochondrial function. Severe or fatal arrhythmias and heart failure are quite frequent. the aromatic diamidine pentamidine acts via inhibition of hERG channel trafficking. Pentamidine has no acute effects on currents produced by hERG, KvLQT1/mink, Kv4.3, or SCNA5. After overnight exposure, however, pentamidine reduces hERG currents and inhibited trafficking and maturation of hERG with IC50 values of 5 to 8 µM similar to therapeutic concentrations.

Clarithromycin is an antibiotic made from erythromycin is chemically known as 6-O-methylerythromycin. It is in the macrolide class and works by stopping the making of protein by some bacteria. It causes QT prolongation or ventricular cardiac arrhythmias, including torsade de pointes.

Erythromycin is an antibiotic with common side effects that include serious side effects arrhythmia with prolonged QT intervals including torsades de pointes.

Grepafloxacin is an oral broad-spectrum fluoroquinolone antibacterial agent used to treat bacterial infections. Grepafloxacin was withdrawn worldwide from markets in 1999, owing to its side effect of lengthening the QT interval on the electrocardiogram, leading to cardiac events and sudden death.

Sparfloxacin is a fluoroquinolone broad-spectrum antibiotic used in the treatment of bacterial infections. It has a controversial safety profile. The use of sparfloxacin is contraindicated in patients with known QTc prolongation and in patients treated concomitantly with class IA or III antiarrhythmic drugs. In a study, the maximum plasma concentration (Cmax) after the 1200- and 1600-mg doses was lower than would be expected for a linear dose relationship. This was also the case with the mean increase and mean maximum increase in QTc interval. Increases in the QTc interval correlated well with $C_{max}$ but not with AUCo-infinity.

Curcumin (diferuloylmethane) is a bright yellow chemical produced by some plants. It is the principal curcuminoid of turmeric (*Curcuma longa*) and exerts antioxidant, anti-inflammatory, antiviral, antibacterial, antifungal, and anti-tumor activities. In whole-cell patch-clamp experiments, curcumin inhibited hERG K+ currents in HEK293 cells stably expressing hERG channels in a dose-dependent manner, with IC50 value of 5.55 µM. The deactivation, inactivation and the recovery time from inactivation of hERG channels were significantly changed by acute treatment of 10 µM curcumin.

Antiarrhythmics.

Antiarrhythmics are used to suppress abnormal rhythms of the heart (cardiac arrhythmias), such as atrial fibrillation, ventricular tachycardia, and ventricular fibrillation.

Procainamide is an antiarrhythmic class used for the treatment of cardiac arrhythmias. It is classified by the Vaughan Williams classification system as class Ia, and is used for both supraventricular and ventricular arrhythmias. It was also detected that the antiarrhythmic drug procainamide interferes with pacemakers. Because a toxic level of procainamide leads to decrease in ventricular conduction velocity and increase of the ventricular refractory period. This results in a disturbance in the artificial membrane potential and leads to a supraventricular tachycardia, which induces failure of the pacemaker and death. It induces rapid block of the batrachotoxin (BTX)-activated sodium channels of the heart muscle and acts as antagonist to long gating closures Procainamide belongs to the aminobenzamides, which has similar cardiac effects as quinidine it has the same toxicity profile as quinidine Propafenone is a class 1C anti-arrhythmic medication, which treats illnesses associated with rapid heart beats such as atrial and ventricular arrhythmias and works by slowing the influx of sodium ions into the cardiac muscle cells, causing a decrease in excitability of the cells. Propafenone is more selective for cells with a high rate, but also blocks normal cells more than class Ia or Ib. Propafenone differs from the prototypical class Ic antiarrhythmic in that it has additional activity as a beta-adrenergic blocker, which can cause bradycardia.

Methanesulphonanilide (E-4031) is an experimental class III antiarrhythmic drug that blocks potassium channels of class III antiarrhythmic drug. E-4031 acts on a specific class of voltage-gated potassium channels mainly found in the heart, the hERG channels. hERG channels (Kv11.1) mediate the IKr current, which repolarizes the myocardial cells. The hERG channel is encoded by ether-a-go-go related gene (hERG). E-4031 blocks hERG-type potassium channels by binding to the open channels. Its structural target within the hERG-channel is unclear, but some other methanesulfonanilide class III antiarrhythmic drugs are known to bind to the S6 domain or C-terminal of the hERG-channel. As E-4031 can prolong the QT-interval, it can cause lethal arrhythmias. So far, one clinical trial has been conducted to test the effect of E-4031 on prolongation of the QT-interval.

Amiodarone is a class III antiarrhythmic for ventricular fibrillation or tachycardia. prolongs phase 3 of the cardiac action potential. Amiodarone is an antiarrhythmic agent known to cause prolongation of action potential duration, which is reflected in the electrocardiogram as a prolongation of the QT. Amiodarone has multiple effects on myocardial depolarization and repolarization that make it an extremely effective antiarrhythmic drug. Its primary effect is to block the potassium channels, but it can also block sodium and calcium channels and the beta and alpha adrenergic receptors. Amiodarone significantly prolongs the QT interval and the QTc value.

Dronedarone is a benzofuran derivative related to amiodarone, is a drug used mainly for cardiac arrhythmias (approved by the FDA in 2009). It is a "multichannel blocker", however, it is unclear which channel(s) play a pivotal role in its success. Dronedarone's actions at the cellular level are controversial with most studies suggesting an inhibition in multiple outward potassium currents including rapid delayed rectifier, slow delayed rectifier and ACh-activated inward rectifier. It is also believed to reduce inward rapid Na current and L-type Ca channels. The reduction in K current in some studies was shown to be due to the inhibition of K-ACh channel or associated GTP-binding proteins. A reduction of K+ current by 69% led to increased AP duration and increased effective refractory periods, Displays amiodarone-like class III antiarrhythmic activity in vitro and in clinical trials. The drug also appears to exhibit activity in each of the 4 Vaughan-Williams antiarrhythmic classes. Contraindicated in Concomitant use of drugs or herbal products that prolong the QT interval and may induce Torsade de Pointes QTc Bazett interval ≥500 ms, or use with drugs or herbal supplements that prolong QT interval or increase risk of torsades de points (Class I or III antiarrhythmic agents, phenothiazines, tricyclic antidepressants, certain oral macrolides, ephedra).

Disopyramide is an antiarrhythmic medication used in the treatment of ventricular tachycardia. It is a sodium channel blocker and therefore classified as a Class 1a anti-arrhythmic agent. Disopyramide's Class 1a activity is similar to that of quinidine in that it targets sodium channels to inhibit conduction. Disopyramide depresses the increase in sodium permeability of the cardiac Myocyte during Phase 0 of the cardiac action potential, in turn decreasing the inward sodium current. This results in an increased threshold for excitation and a decreased upstroke velocity Disopyramide prolongs the PR interval by lengthening both the QRS and P wave duration. Concern about disopyramide has been the hypothetical potential for inducing sudden death from its type 1 anti-arrhythmic effects.

Dofetilide is a class III antiarrhythmic agent. Due to the pro-arrhythmic potential of dofetilide, it is only available by prescription from physicians who have undergone specific training in the risks of treatment with dofetilide. In addition, it is only available by mail order or through specially trained local pharmacies Dofetilide works by selectively blocking the rapid component of the delayed rectifier outward potassium current. There is a dose-dependent increase in the QT interval and the corrected QT interval (QTc). Because of this, many practitioners will initiate dofetilide therapy only on individuals under telemetry monitoring or if serial EKG measurements of QT and QTc can be performed.

Sotalol is a non-selective competitive beta-adrenergic receptor blocker that also exhibits Class III antiarrhythmic properties. The U.S. Food and Drug Administration advises that sotalol only be used for serious arrhythmias, because its prolongation of the QT interval carries a small risk of life-threatening torsade de pointes. Sotalol also acts on potassium channels and causes a delay in relaxation of the ventricles. By blocking these potassium channels, sotalol inhibits efflux of K+ ions, which results in an increase in the time before another electrical signal can be generated in ventricular myocytes. This increase in the period before a new signal for contraction is generated.

Ibutilide is a Class III antiarrhythmic agent that is indicated for acute cardioconversion of atrial fibrillation and atrial flutter and prolongs action potential and refractory period of myocardial cells. Because of its Class III antiarrhythmic activity, there should not be concomitant administration of Class Ia and Class III agents. Unlike most other Class III antiarrhythmic drugs, ibutilide does not produce its prolongation of action potential via blockade of cardiac delayed rectifier of potassium current, nor does it have a sodium-blocking, antiadrenergic, and calcium blocking activity that other Class III agents possess. Thus, it is often referred as a "pure" Class III antiarrhythmic drug. Ibutilide, like other class III antiarrhythmic drugs, blocks delayed rectified potassium current. It does have action on the slow sodium channel and promotes the influx of sodium through these slow channels. Like other antiarrhythmics, ibutilide can lead to abnormal heart rhythms due to its ability to prolong the QT interval, which can lead to the potentially fatal abnormal heart rhythm known as torsades de pointes. The drug is contraindicated in patients that are likely to develop abnormal heart rhythms; persons that have had polymorphic ventricular tachycardia in the past, have a long QT interval, sick sinus syndrome, or a recent myocardial infarction, among others.

Dopamine Receptor Antagonists.

A dopamine antagonist (antidopaminergic) is a type of drug that blocks dopamine receptors by receptor antagonism. Most antipsychotics are dopamine antagonists, and as such they have found use in treating schizophrenia, bipolar disorder, and stimulant psychosis. Several other dopamine antagonists are antiemetics used in the treatment of nausea and vomiting.

Droperidol is an antidopaminergic butyrophenone, used as an antiemetic and antipsychotic, and is a potent D2 (dopamine receptor) antagonist with some histamine and serotonin antagonist activity. There are concerns about QT prolongation and torsades de pointes. The evidence for this is disputed, with 9 reported cases of torsades in 30 years and all of those having received doses in excess of 5 mg. QT prolongation is a dose-related effect, and it appears that droperidol is not a significant risk in low doses, however, prolongation of QT interval leads to torsades de pointes.

Domperidone is a peripherally selective dopamine D2 receptor antagonist that is a drug useful in Parkinson's disease, caution is needed due to the cardiotoxic side effects of domperidone especially when given intravenously, in elderly people and in high doses (>30 mg per day). A clinical sign of domperidone's potential toxicity to the heart is the prolongation (lengthening) of the QT interval (a segment of the heart's electrical pattern). Domperidone use is associated with an increased risk of sudden cardiac death (by 70%) most likely through its prolonging effect of the cardiac QT interval and ventricular arrhythmias. The cause is thought to be blockade of hERG voltage-gated potassium channels. The risks are dose-dependent, and appear to be greatest with high/very high doses via intravenous administration and in the elderly, as well as with drugs that interact with domperidone and increase its circulating concentrations (namely CYP3A4 inhibitors). Conflicting reports exist, however. In neonates and infants, QT prolongation is controversial and uncertain.

Anticancer Agents.

Doxorubicin and anthracycline prolongation of QTc, increased QT dispersion and development of late potentials are indicative of doxorubicin-induced abnormal ventricular depolarization and repolarization. QT dispersion and late potentials are both known to be associated with increased risk of serious ventricular dysrhythmias and sudden death in various cardiac diseases.

Arsenic trioxide is a anti-leukemic can prolong the QTc interval. Cardiac Conduction Abnormalities: Before initiating therapy, perform a 12-lead ECG, assess serum electrolytes and creatinine, correct preexisting electrolyte abnormalities, and consider discontinuing drugs known to prolong QT interval. Arsenic trioxide can cause QT interval prolongation and complete atrioventricular block. QT prolongation can lead to a torsade de pointes-type ventricular arrhythmia, which can be fatal. The risk of torsade de pointes is related to the extent of QT prolongation, concomitant administration of QT prolonging drugs, a history of torsade de pointes, preexisting QT interval prolongation, congestive heart failure, administration of potassium-wasting diuretics, or other conditions that result in hypokalemia or hypomagnesemia. One patient (also receiving amphotericin B) had torsade de pointes during induction therapy for relapsed APL with arsenic trioxide. Arsenic trioxide ($As_2O_3$) used in the treatment of acute promyelocytic leukemia reduced hERG/IKr currents not by direct block, but by inhibiting the processing of hERG protein in the endoplasmic reticulum (ER) thereby decreasing surface expression of hERG.

Opioids.

Levomethadyl is a levo isomer of α-methadyl acetatea synthetic opioid similar in structure to methadone. It has a long duration of action due to its active metabolites. In 2001, levacetylmethadol was removed from the European market due to reports of life-threatening ventricular rhythm disorders.

Methadone is an opioid used to treat pain and drug addiction. Serious risks include opioid abuse and heart arrhythmia may also occur including prolonged QT. The number of deaths in the United States involving methadone poisoning was 4,418 in 2011, which was 26% of total deaths from opioid poisoning.

Hypolipidemic Agents.

Lovostatin is a drug used for lowering cholesterol an inhibitor of 3-hydroxy-3-methylglutaryl-coenzyme A reductase (HMG-CoA reductase), an enzyme that catalyzes the conversion of HMG-CoA to mevalonate. Mevalonate is a required building block for cholesterol biosynthesis and lovastatin interferes with its production by acting as a reversible competitive inhibitor for HMG-CoA, which binds to the HMG-CoA reductase. QTc prolongation associated with antipsychotic medication occurs in a dose-dependent manner. The addition of lovastatin causes an increase in plasma quetiapine levels through competitive inhibition of the cytochrome P(450) (CYP) isoenzyme 3A4. This highlights the potential for a drug interaction between quetiapine and lovastatin leading to QTc prolongation during the management of dysipidemia in patients with schizophrenia.

Probucol is an anti-hyperlipidemic drug initially developed in the treatment of coronary artery disease. Probucol is associated with QT interval prolongation. Probucol aggravates long QT syndrome associated with a novel missense mutation M124T in the N-terminus of HERG.

Human Ether-a-go-go-Related Gene (hERG) Potassium Channel Anti-Blockade by Liposome and Fragments.

Potassium channels conduct the rapid component of the delayed rectifier potassium current, Kir, which is crucial for repolarization of cardiac action potentials. A reduction in hERG currents due to either genetic defects or adverse drug effects can lead to hereditary or acquired long QT syndromes characterized by action potential prolongation, lengthening of the QT interval on the surface ECG, and an increased risk for "torsade de pointes" arrhythmias and sudden death. This undesirable side effect of non-antiarrhythmic compounds has prompted the withdrawal of drugs from the market. Studies on mechanisms of hERG channel inhibition provide significant insights into the molecular factors that determine state-, voltage-, and use-dependency of hERG current block. Mutations altering properties of the high-affinity drug binding site in hERG and its interaction with drug molecules cause current increase and hereditary short QT syndrome with a high risk for life-threatening arrhythmias. (Thomas D1, 2006).

Another member of the inward-rectifier family of potassium channels is the prokaryotic KirBac1.1 channel. The structure of the Kir channel assembly in the closed state, when refined to a resolution of 3.65 angstroms contains a main activation gate and structural elements involved in gating. On the basis of structural evidence, gating involves coupling between the intracellular and membrane domains suggesting that initiation of gating by membrane or intracellular signals represents different entry points to a common mechanistic pathway. (Kuo, A 2003).

Channelopathies.

The human ether-à-go-go gene related cardiac tetrameric potassium channel. when mutated can render patients sensitive to over 163 drugs which may inhibit ion conduction and deregulate action potentials. Prolongation of the action potential follows effects in the potassium channel. Ion channel active drugs may directly increase the QTc interval, and increase the risk of torsade de point and sudden cardiac death. Exacerbation of cardiomyocyte potassium channel sensitivity to drugs may also be associated with metabolic diseased states including diabetes or may be of idiopathic origin.

For these reasons, evaluation of drug effects on cardiomyocyte potassium channel function is a critical step during drug development, and when serious, may be an obstacle to regulatory approval. In whole-cell patch-clamp experiments, curcumin inhibited hERG $K^+$ currents in HEK293 cells stably expressing hERG channels in a dose-dependent manner, with IC50 value of 5.55 μM. The deactivation, inactivation, and the recovery time from inactivation of hERG channels were significantly changed by acute treatment of 10 μM curcumin. Incubation of 20 μM curcumin for 24 h reduced the HEK293 cell viability. Intravenous injection of 20 mg of curcumin in rabbits did not affect the cardiac repolarization manifested by QTc values. (Hu CW 2012). These molecules are specific liposomes, or components of liposomes which were initially bound to lipophilic drugs to permit intravenous solubility at physiological conditions, and reduce adverse events. The loci of action appears to be in intra-channel ion selectivity or gating site(s) controlling potassium ion movement: a key functional component of regulation of action potentials which lead downstream to myocyte contraction.

The mechanism of human ether-à-go-go related gene channels blocade may be analogous to the effects of externally applied quaternary ammonium derivatives which indirectly may suggest the mechanism of action of the anti-blockading effect of the DMPC/DMPG liposome or its metabolites. The inhibitory constants and the relative binding energies for channel inhibition indicate that more hydrophobic quaternary ammoniums have higher affinity blockade while cation-π interactions or size effects are not a deterministic factor in channel inhibition by quaternary ammoniums. Also hydrophobic quaternary ammoniums either with a longer tail group or with a bigger head group than tetraethylammonium permeate the cell membrane to easily access the high-affinity internal binding site in the gene channel and exert a stronger blockade.

Although these data suggest that the basis for the ameliorating effect liposome, or its components is the higher competitive affinity for binding sites by the, DMPC and DMPG compared to QTc prolonging drugs, its constitutive lack of ion transport modulation, i.e. liposome or its fragments do not impede K+ ion transport indicates that By way of explanation, and in no way a limitation of these claims, these data suggest that the basis for the ameliorating effect liposome, or its components, is the higher competitive affinity for binding sites by the DMPC and DMPG compared to QTc prolonging drugs, its constitutive lack of ion transport modulation, i.e., liposome, or its fragments, do not impede K+ ion transport and indicates that the site of the mechanism of DMPC or DMPG protection may be in the selectivity segment of the channel or in the hydration surrounding the ion.

Additionally, based upon these hERG channel data the structures of these liposome components may be informative for designing or selecting other molecules to prevent drug induced cardiac arrhythmias.

This study provides additional information as to the QTc modulating effects by drugs, induced in cardiac myocyte potassium channels, and mitigation by liposomes and liposomal constituents. The latter molecules present an opportunity to probe the K+ channels as targets for pharmacological mitigation of drug-induced channelopathies.

Evaluation of the protective effect of DMPC, DMPG, DMPC/DMPG, LysoPG and LysoPC against hERG inhibition by Nilotinib.

Purpose of the study: The purpose of this study is to evaluate in vitro the protective effect of DMPC, DMPG, DMPC/DMPG, LysoPG and LysoPC on the rapidly activating delayed-rectifier potassium selective current ($I_{Kr}$) generated under normoxic conditions in stably transfected Human Embryonic Kidney cells (HEK 293 cells). This study was designed as a screen and does not require QA involvement (non-GLP-compliant).

Test Articles:
1—DMPC
2—DMPG
3—DMPC/DMPG 90:9
4-14:0 LysoPC
5-14:0 LysoPG
6—DMPC+Nilotinib (0.1 µM)
7—DMPG+Nilotinib (0.1 µM)
8—DMPC/DMPG 90:9+Nilotinib (0.1 µM)
9—14:0 LysoPC+Nilotinib (0.1 µM)
10—14:0 LysoPG+Nilotinib (0.1 µM)

Test System: hERG-expressing HEK 293 transfected cell line. Test performed: Whole-cell patch-clamp current acquisition and analysis. Experimental Temperature: 35±2° C.

Application of test articles: 5 minutes of exposure to each concentration in presence of closed circuit perfusion (2 mL/min). 5 minutes for washout periods in presence of a flow-through perfusion (2 mL/min) in addition to a closed circuit perfusion (2 mL/min). The positive control (Nilotinib, 0.05 µg/mL) was added to naive cells obtained from the same cell line and same passage for a period of 5 minutes in presence of a closed circuit perfusion (2 mL/min).

Cells were under continuous stimulation of the pulses protocol throughout the experiments and cell currents were recorded after 5 minutes of exposure to each condition.

Original data acquisition design: Acquisition Rate(s): 1.0 kHz.

Design for acquisition when testing the compound or the vehicle/solvent equivalent:
1 recording made in baseline condition
1 recording made in the presence of concentration 1
Design for acquisition when testing the positive control:
1 recording made in baseline condition
1 recording made in the presence of the positive control
n=number of responsive cells patched on which the whole protocol above could be applied.

Statistical analysis: Statistical comparisons were made using paired Student's t-tests. The currents recorded obtained on day 2, 3 and 4 were statistically compared to the currents recorded on day 1.

The currents recorded after the positive control (nilotinib alone) exposure were compared to the currents recorded in baseline conditions.

Differences were considered significant when p 0.05.

Exclusion Criteria:
1. Timeframe of drug exposure not respected
2. Instability of the seal
3. No tail current generated by the patched cell
4. No significant effect of the positive control
5. More than 10% variability in capacitance transient amplitude over the duration of the Study.

Effect of the Test Articles on whole-cell IKr hERG currents. Whole-cell currents elicited during a voltage pulse were recorded in baseline conditions and following the application of the selected concentration of test article. The cells were depolarized for one second from the holding potential (−80 mV) to a maximum value of +40 mV, starting at −40 mV and progressing in 10 mV increments. The membrane potential was then repolarized to −55 mV for one second, and finally returned to −80 mV.

Whole-cell tail current amplitude was measured at a holding potential of −55 mV, following activation of the current from −40 to +40 mV. Current amplitude was measured at the maximum (peak) of this tail current. Current density was obtained by dividing current amplitude by cell capacitance measured prior to capacitive transient minimization.

Current run-down and solvent effect correction. All data points presented in this Study Report have been corrected for solvent effect and time-dependent current run-down. Current run-down and solvent effects were measured simultaneously by applying the experimental design in test-article free conditions over the same time frame as was done with the test article. The loss in current amplitude measured during these so-called vehicle experiments (representing both solvent effects and time-dependent run-down) was subtracted from the loss of amplitude measured in the presence of the test article to isolate the effect of the test article, apart from the effect of the solvent and the inevitable run-down in current amplitude over time.

TABLE 1

Effect of DMPC, DMPC + Nilotinib and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPC | 0.863 | 1.056 | 0.056 | 0.423 | 3 |
| Nilotinib, 0.1 µM | 0.308 | 0.459* | 0.070 | 0.016 | 3 |
| DMPC + Nilotinib, 0.1 µM | 0.836 | 1.029 | 0.023 | 0.328 | 3 |

FIG. 1 is a graph that shows the effect of DMPC, DMPC+Nilotinib and Nilotinib on hERG current density from transfected HEK 293 cells.

TABLE 2

Effect of DMPG, DMPG + Nilotinib and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPG | 0.800 | 0.994 | 0.044 | 0.901 | 3 |

TABLE 2-continued

Effect of DMPG, DMPG + Nilotinib and Nilotinib on hERG current density from transfected HEK 293 cells.

| | Normalized Current Density | Corrected Normalized Current Density | SEM | p value | n = |
|---|---|---|---|---|---|
| Nilotinib, 0.1 µM | 0.308 | 0.459* | 0.070 | 0.016 | 3 |
| DMPG + Nilotinib, 0.1 µM | 0.743 | 0.936 | 0.067 | 0.437 | 3 |

Figure 2:
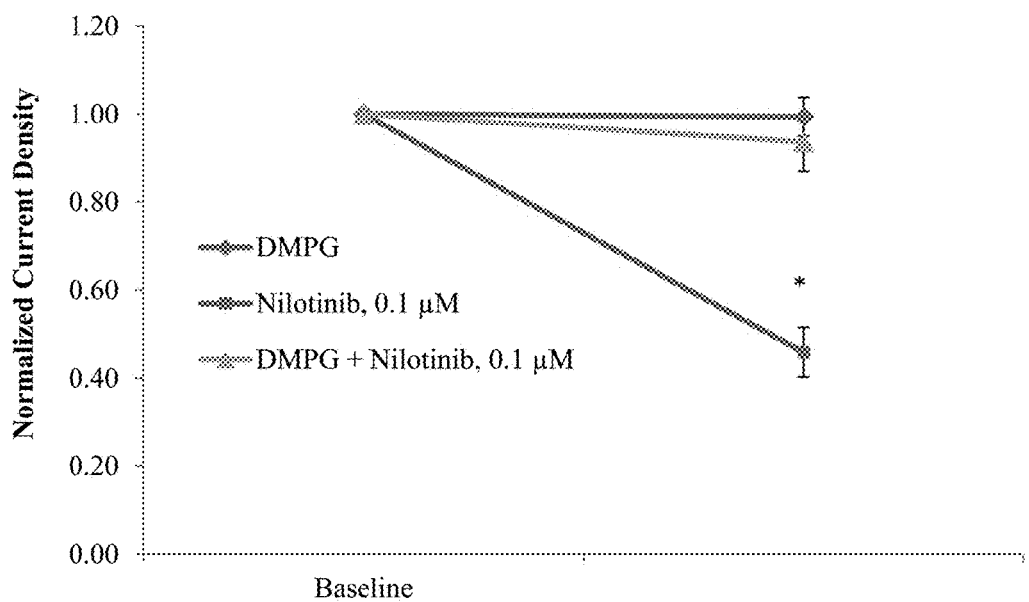
FIG. 2 is a graph that shows the effect of DMPG, DMPG+Nilotinib and Nilotinib on hERG current density from transfected HEK 293 cells.

FIG. 2 is a graph that shows the effect of DMPG, DMPG+Nilotinib and Nilotinib on hERG current density from transfected HEK 293 cells.

TABLE 3

Effect of DMPC/DMPG, DMPC/DMPG + Nilotinib and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPC-DMPG | 0.871 | 1.064 | 0.127 | 0.647 | 4 |
| Nilotinib, 0.1 µM | 0.308 | 0.459* | 0.070 | 0.016 | 3 |
| DMPC/DMPG + Nilotinib, 0.1 µM | 0.773 | 0.966 | 0.098 | 0.754 | 4 |

Figure 3:
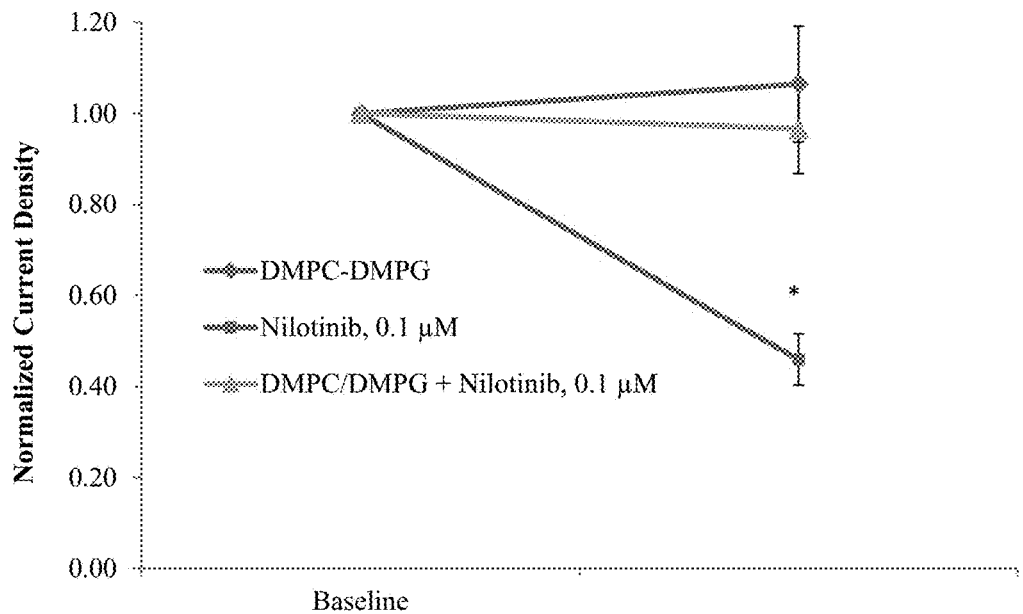
FIG. 3 is a graph that shows the effect of DMPC/DMPG, DMPC/DMPG+Nilotinib and Nilotinib on hERG current density from transfected HEK 293 cells.

FIG. 3 is a graph that shows the effect of DMPC/DMPG, DMPC/DMPG+Nilotinib and Nilotinib on hERG current density from transfected HEK 293 cells.

TABLE 4

Effect of LysoPC, LysoPC + Nilotinib and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| LysoPC | 0.647 | 0.840* | 0.040 | 0.028 | 4 |
| Nilotinib, 0.1 µM | 0.308 | 0.459* | 0.070 | 0.016 | 3 |
| LysoPC + Nilotinib, 0.1 µM | 0.865 | 1.097 | 0.055 | 0.553 | 3 |

Figure 4:
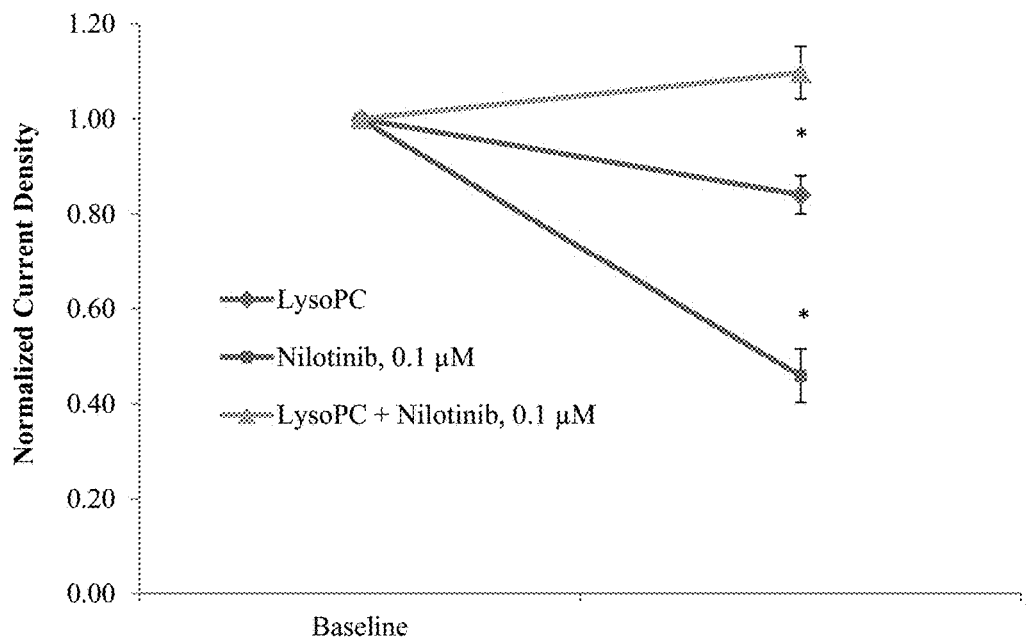
FIG. 4 is a graph that shows the effect of LysoPC, LysoPC+Nilotinib and Nilotinib on hERG current density from transfected HEK 293 cells.

FIG. 4 is a graph that shows the effect of LysoPC, LysoPC+Nilotinib and Nilotinib on hERG current density from transfected HEK 293 cells.

TABLE 5

Effect of LysoPG, LysoPG + Nilotinib and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| 14:0 LysoPG, 0.45 µg/mL | 0.930 | 1.124 | 0.128 | 0.435 | 3 |
| Nilotinib, 0.1 µM | 0.308 | 0.459* | 0.070 | 0.016 | 3 |
| 14:0 LysoPG + Nilotinib, 0.1 µM | 0.743 | 0.936 | 0.067 | 0.437 | 3 |

Figure 5:
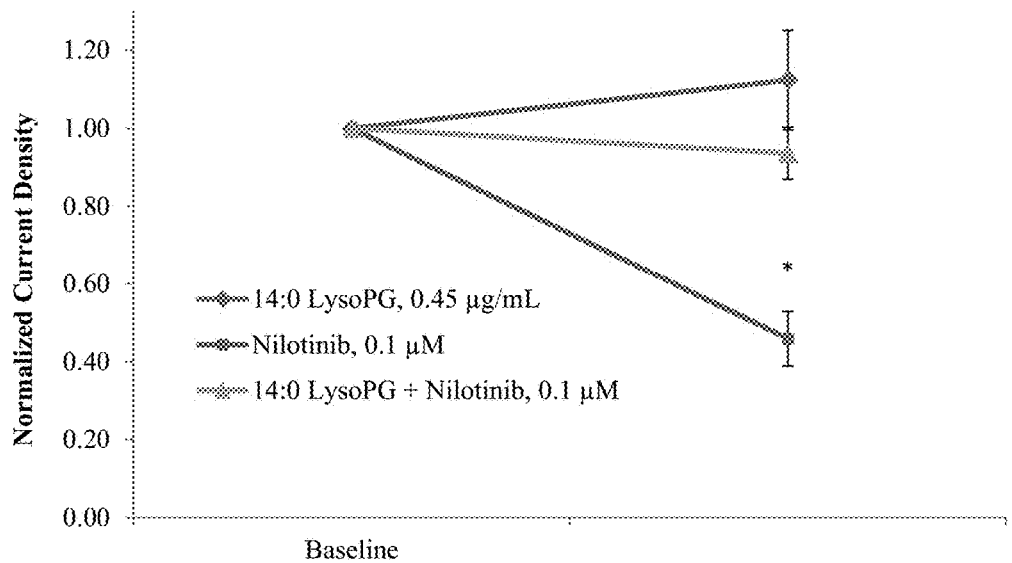
FIG. 5 is a graph that shows the effect of LysoPG, LysoPG+Nilotinib and Nilotinib on hERG current density from transfected HEK 293 cells.

FIG. 5 is a graph that shows the effect of LysoPG, LysoPG+Nilotinib and Nilotinib on hERG current density from transfected HEK 293 cells.

This study aimed at quantifying the protective effect of DMPC, DMPG, DMPC/DMPG, LysoPG and LysoPC against the inhibition of the rapidly activating delayed-rectifier potassium selective current (IKr) generated under normoxic conditions in stably transfected Human Embryonic Kidney (HEK) 293 cells caused by the Nilotinib.

All data points presented in this study have been corrected for solvent effects and time-dependent current run-down. These two parameters were evaluated by applying exactly the same experimental design to the vehicle as that done with the test articles. The currents were measured over the same time course as was done in the presence of the test article. The values obtained, representing both solvent effects and time-dependent run-down, were used to correct the effect of the test articles, if any. This ensures that changes attributable to time or the solvent are not mistakenly attributed to the test articles.

DMPC, DMPG, DMPC/DMPG and LysoPG alone did not cause any inhibition of the hERG tail current density (n=3). LysoPC alone caused 16% of inhibition of the hERG tail current density (n=4).

Nilotinib alone, formulated in DMSO at 0.1 µM, caused 54.1% of inhibition of the hERG tail current (n=3). The inhibition observed is in line with previous data generated in identical conditions, and agrees with reported inhibition values for this compound.

Nilotinib when formulated in an aqueous solution containing DMPC, DMPG, DMPC/DMPC, LysoPG or LysoPC (ratio 1:9) did not cause any inhibition of the hERG tail current.

These data suggest that co-formulating Nilotinib with DMPC, DMPG, DMPC/DMPC, LysoPG and LysoPC protects against hERG inhibition caused by Nilotinib.

In this study, the DMPC+Nilotinib, DMPG+Nilotinib, DMPC/DMPC+Nilotinib, LysoPG+Nilotinib or LysoPC+Nilotinib were all formulated using the same method. The appropriate amount of Nilotinib powder was dissolved in an aqueous solution containing either DMPC, DMPG, DMPC/DMPC, LysoPG or LysoPC (ratio 9:1). The solution was vortexed for 10 minutes before being used in the patch-clamp assay.

In contrast, the Nilotinib used for the cells exposed to Nilotinib alone was dissolved in DMSO. Additional studies were conducted to determine whether the difference in hERG inhibition between DMSO-formulated Nilotinib and lipid-co-formulated Nilotinib resulted from the different formulations (aqueous or DMSO-based).

Steps for the Study:

| Step 1 | Step 2 | Step 3 | Step 4 |
|---|---|---|---|
| Baseline recording | TA* added into the experimental chamber | 5 minutes exposure time | TA recording |

*TA = 1 - DMPC (in aqueous solution) 2 - DMPG (in aqueous solution) 3 - DMPC/DMPG 90:9 (in aqueous solution) 4 - 14:0 LysoPC (in aqueous solution) 5 - 14:0 LysoPG (in aqueous solution) 6 - DMPC + Nilotinib (0.1 µM) (in aqueous solution) 7 - DMPG + Nilotinib (0.1 µM) (in aqueous solution) 8 - DMPC/DMPG 90:9 + Nilotinib (0.1 µM) (in aqueous solution) 9 - 14:0 LysoPC + Nilotinib (0.1 µM) (in aqueous solution) 10 - 14:0 LysoPG + Nilotinib (0.1 µM) (in aqueous solution) 11 - Nilotinib alone (in DMSO)

Amongst the mechanisms considered to explain the protection of hERG currents were the possibility that DMPC/DMPG or the Lyso-variants quenched the Nilotinib at the moment of formulation, essentially preventing it from getting into the channel at its receptor site. Another possibility was that Nilotinib was less soluble in an aqueous solution, and therefore was incompletely solubilized at 0.1 µM.

To test both hypotheses, Nilotinib was formulated in DMSO and added into the experimental chamber following the addition of the DMPC or DMPG. This was based on the principle that 1—adding DMPC/DMPG alone, followed by DMSO-formulated Nilotinib, would eliminate the possibility of early quenching of Nilotinib by the lysosome; and 2—that DMSO would maintain the solubility of Nilotinib (the "Nilotinib-only" inhibition of hERG was observed when DMSO-formulated Nilotinib was added to the cells).

Steps for the Following Data

| Step 1 | Step 2 | Step 3 | Step 4 | Step 5 | Step 6 |
|---|---|---|---|---|---|
| Baseline recording | DMPC or DMPG added into the experimental chamber | 5 minutes exposure time | DMPC or DMPG recording | Nilotinib in DMSO added into the experimental chamber | DMPC or DMPG + Nilotinib (in DMSO) recording |

TABLE 6

Effect of DMPC, DMPC + Nilotinib, DMPC + Nilotinib (in DMSO) and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPC | 0.863 | 1.056 | 0.056 | 0.423 | 3 |
| Nilotinib, 0.1 μM | 0.308 | 0.459* | 0.070 | 0.016 | 3 |
| DMPC + Nilotinib, 0.1 μM (Aqueous) | 0.836 | 1.029 | 0.023 | 0.328 | 3 |
| DMPC + Nilotinib (in DMSO), 0.1 μM | 0.164 | 0.358* | 0.020 | 0.019 | 2 |

Figure 6:
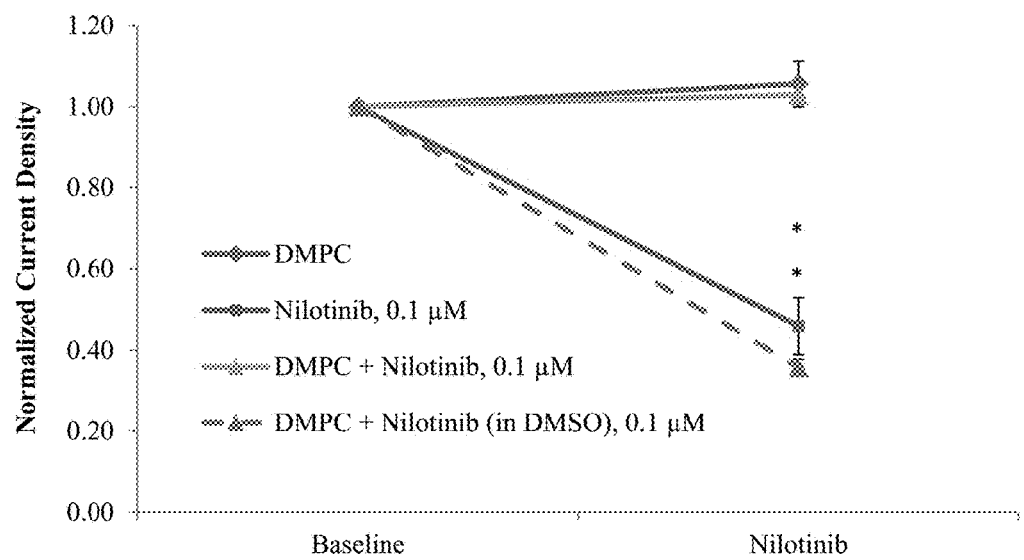
FIG. 6 is a graph that shows the effect of DMPC, DMPC+Nilotinib, DMPC+Nilotinib (in DMSO) and Nilotinib on hERG current density from transfected HEK 293 cells.

FIG. 6 is a graph that shows the effect of DMPC, DMPC+Nilotinib, DMPC+Nilotinib (in DMSO) and Nilotinib on hERG current density from transfected HEK 293 cells.

TABLE 7

Effect of DMPG, DMPG + Nilotinib, DMPG + Nilotinib (in DMSO) and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPG | 0.800 | 0.994 | 0.044 | 0.901 | 3 |
| Nilotinib, 0.1 μM | 0.308 | 0.459* | 0.070 | 0.016 | 3 |
| DMPG + Nilotinib, 0.1 μM | 0.743 | 0.936 | 0.067 | 0.437 | 3 |
| DMPG + Nilotinib (in DMSO), 0.1 μM | 0.630 | 0.823 | 0.290 | 0.651 | 2 |

Figure 7:
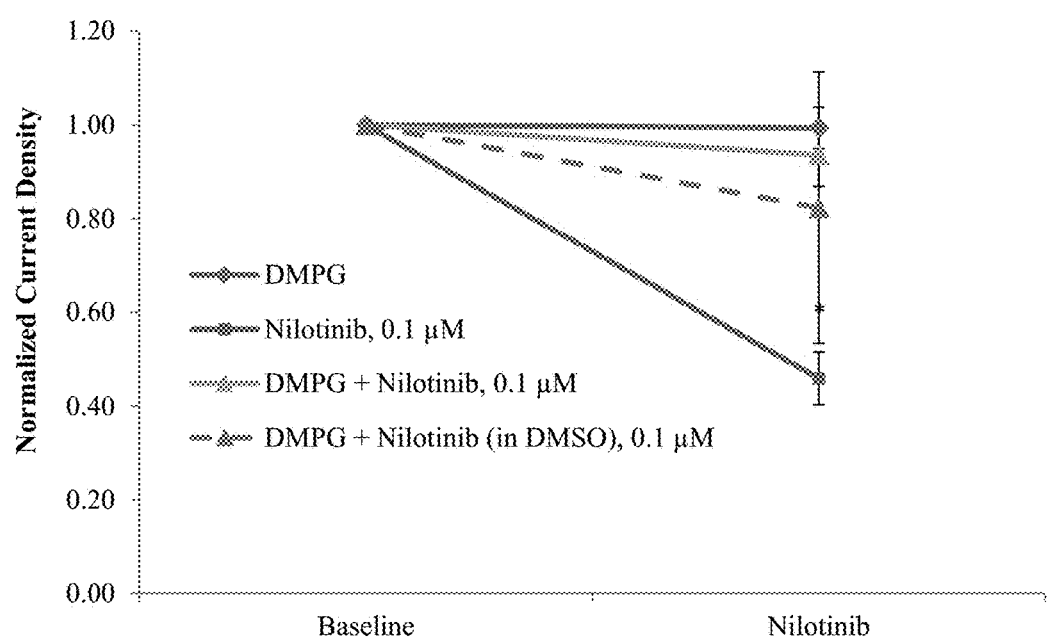
FIG. 7 is a graph that shows the effect of DMPG, DMPG+Nilotinib, DMPG+Nilotinib (in DMSO) and Nilotinib on hERG current density from transfected HEK 293 cells.

FIG. 7 is a graph that shows the effect of DMPG, DMPG+Nilotinib, DMPG+Nilotinib (in DMSO) and Nilotinib on hERG current density from transfected HEK 293 cells.

Figure 8:
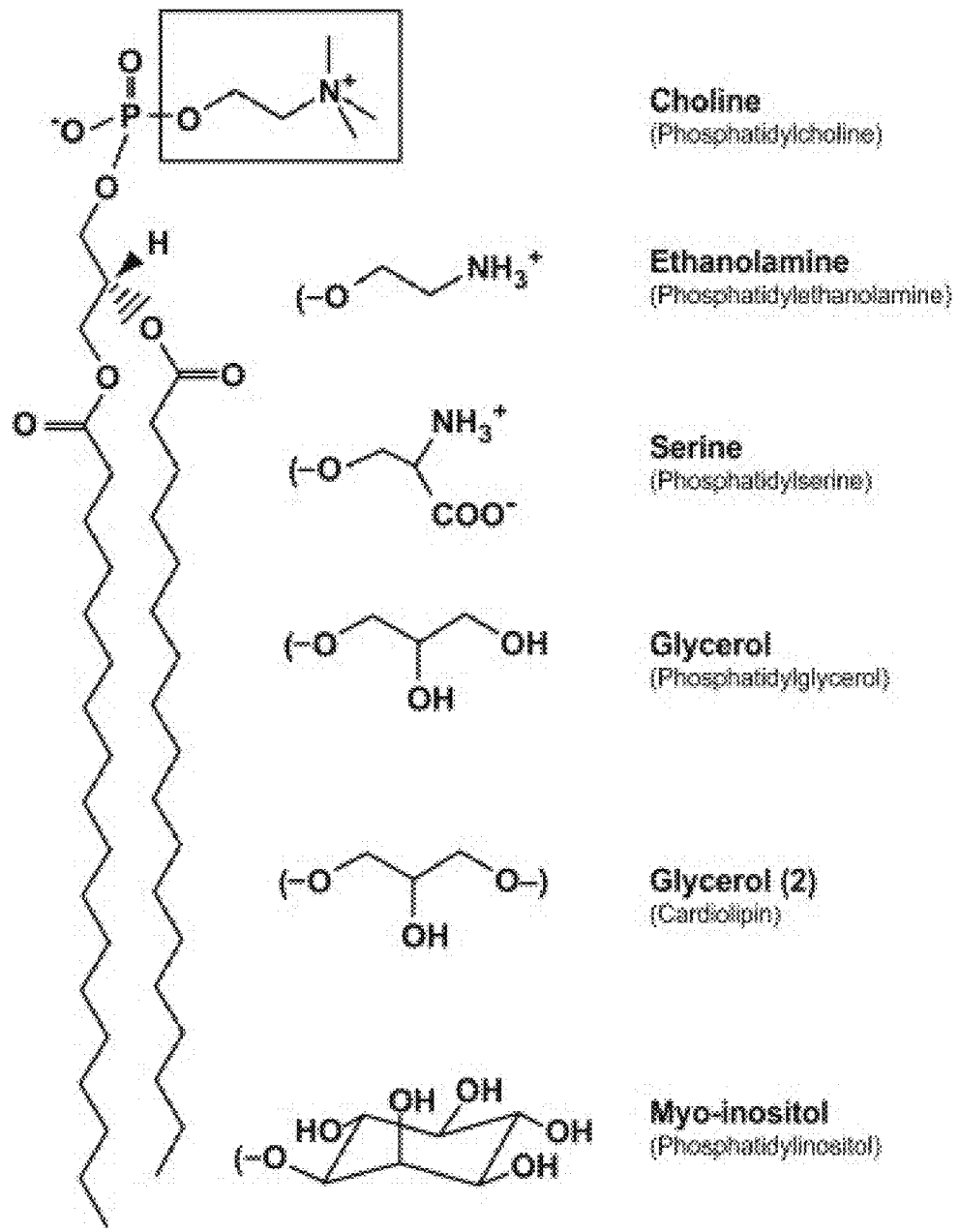
FIG. 8 shows the structure of glycerophosphate-based lipids for use with the present invention.

FIG. 8 shows the structure of glycerophosphate-based lipids for use with the present invention. The lipid structure shown is 1,2 distearoyl-sn-glycerol-3-phosphocholine or phosphatidylcholine (PC). Substitution of choline in the box with the head groups shown on the right forms the other phospholipid structures. Cardiolipin (CL) is also referred to as diphosphatidylglycerol since it contains two PAs joined by a glycerol.

Table 8 shows examples of fatty acids for use with the present invention.

Examples of Unsaturated Fatty Acids

| Common name | Chemical structure | $\Delta^x$ | C:D | n-x |
|---|---|---|---|---|
| Myristoleic acid | $CH_3(CH_2)_3CH = CH(CH_2)_7COOH$ | cis-$\Delta^9$ | 14:1 | n-5 |
| Palmitoleic acid | $CH_3(CH_2)_5CH = CH(CH_2)_7COOH$ | cis-$\Delta^9$ | 16:1 | n-7 |
| Sapienic acid | $CH_3(CH_2)_8CH = CH(CH_2)_4COOH$ | cis-$\Delta^6$ | 16:1 | n-10 |
| Oleic acid | $CH_3(CH_2)_7CH = CH(CH_2)_7COOH$ | cis-$\Delta^9$ | 18:1 | n-9 |
| Elaidic acid | $CH_3(CH_2)_7CH = CH(CH_2)_7COOH$ | trans-$\Delta^9$ | 18:1 | n-9 |
| Vaccenic acid | $CH_3(CH_2)_5CH = CH(CH_2)_9COOH$ | trans-$\Delta^{11}$ | 18:1 | n-7 |
| Linoleic acid | $CH_3(CH_2)_4CH = CHCH_2CH = CH(CH_2)_7COOH$ | cis,cis-$\Delta^9,\Delta^{12}$ | 18:2 | n-6 |
| Linoelaidic acid | $CH_3(CH_2)_4CH = CHCH_2CH = CH(CH_2)_7COOH$ | trans,trans-$\Delta^9,\Delta^{12}$ | 18:2 | n-6 |
| α-Linolenic acid | $CH_3CH_2CH = CHCH_2CH = CHCH_2CH = CH(CH_2)_7COOH$ | cis,cis,cis-$\Delta^9,\Delta^{12},\Delta^{15}$ | 18:3 | n-3 |
| Arachidonic acid | $CH_3(CH_2)_4CH = CHCH_2CH = CHCH_2CH = CHCH_2CH = CH(CH_2)_3COOH^{NIST}$ | cis,cis,cis,cis-$\Delta^5,\Delta^8,\Delta^{11},\Delta^{14}$ | 20:4 | n-6 |
| Eicosapentaenoic acid | $CH_3CH_2CH = CHCH_2CH = CHCH_2CH = CHCH_2CH = CHCH_2CH = CH(CH_2)_3COOH$ | cis,cis,cis,cis,cis-$\Delta^5,\Delta^8,\Delta^{11},\Delta^{14},\Delta^{17}$ | 20:5 | n-3 |
| Erucic acid | $CH_3(CH_2)_7CH = CH(CH_2)_{11}COOH$ | cis-$\Delta^{13}$ | 22:1 | n-9 |
| Docosahexaenoic acid | $CH_3CH_2CH = CHCH_2CH = CHCH_2CH = CHCH_2CH = CHCH_2CH = CHCH_2CH = CH(CH_2)_2COOH$ | cis,cis,cis,cis,cis,cis-$\Delta^4,\Delta^7,\Delta^{10},\Delta^{13},\Delta^{16},\Delta^{19}$ | 22:6 | n-3 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Publication No. 2010/0004549: System and Method of Serial Comparison for Detection of Long QT Syndrome (LQTS).
U.S. Patent Publication No. 2008/0255464: System and Method for Diagnosing and Treating Long QT Syndrome.
U.S. Patent Publication No. 2007/0048284: Cardiac Arrhythmia Treatment Methods.
U.S. Patent Publication No. 2001/00120890: Ion Channel Modulating Activity I.

What is claimed is:

1. A composition consisting of:
one or more pharmacologically active agents provided in an amount that induce a cardiac channelopathy or a condition resulting from the irregularity or alteration in the cardiac pattern selected from QTc, LQT2, LQTS, or torsades de pointes in a subject and one or more lipids provided in an amount sufficient to prevent or reduce the cardiac channelopathy or the condition resulting from the irregularity or alteration in the cardiac pattern caused by the one or more pharmacologically active agents in a formulation, wherein the formulation is dispersed in a pharmaceutically acceptable medium, solvent, or vehicle, wherein the active agent, the lipids, or both are dissolved, dispersed, or suspended in the medium, the solvent, or the vehicle, wherein the lipids reduce or prevent the cardiac channelopathy or a condition resulting from the irregularity or alteration in the cardiac pattern.

2. The composition of claim 1, wherein the one or more pharmacologically active agents is selected from at least one of 5-HT3 antagonists that block serotonin binding, 5-HT4 receptor agonists, histamine antagonists, calcium channel blockers, anti-malarial agents, antipsychotic agents, halodols, antibiotics, anti-arrhythmics, anti-cancer agents, opioids, or hypolipidemic agents.

3. The composition of claim 1, wherein the lipid comprises at least one of a phosphatidylcholine, a phosphatidylethanolamine, a phosphatidylserine, a phosphatidylglycerol, a cardiolipin, a phosphatidylinositol or a precursor thereof.

4. The composition of claim 1, wherein the lipid comprises a lysophosphatidylglycerol, a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine, erucoyl-lysophosphatidylcholine, 1-Myristoyl-2-Hydroxy-sn-Glycero-3-Phosphocholine, 1,2-Dimyristoyl-sn-glycero-3-phosphorylcholine (DMPC), 1,2-Mysteroyl-2-Hydroxy-sn-Glycero-3-[Phospho-rac-(glycerol)], 1,2-Dimyristoyl-sn-glycero-3-phosphorylglycerol (DMPG), DMPC/DMPG, 1-myristoyl-2-hydroxy-sn-glycero-3-phospho-(1'-rac-glycerol) (LysoPG), or 1-myristoyl-2-hydroxy-sn-glycero-3-phosphocholine (LysoPC).

5. The composition of claim 1, wherein the active agent drug is selected from at least one of crizotinib, nilotinib, terfenadine, astemizole, gripafloxacin, terodilene, droperidole, lidoflazine, levomethadyl, sertindoyle or cisapride.

6. The composition of claim 1, wherein the composition is adapted for enteral, parenteral, intravenous, intraperitoneal, cutaneous, subcutaneous, pulmonary, rectal, vaginal, or oral administration.

7. The composition of claim 1, wherein the active agent is provided in a lipid that is formed into a liposome, wherein the lipid is selected from at least one of phosphatidylcholine, lysolecithin, lysophosphatidylethanol-amine, phosphatidylserine, phosphatidylinositol, sphingomyelin, phosphatidylethanolamine, cardiolipin, phosphatidic acid, cerebrosides, dicetylphosphate, phosphatidylcholine, and dipalmitoylphosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, or diacylglycerol succinate.

8. The composition of claim 1, wherein the active agent is selected from Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Curcumin, Crizotinib, Dabrafenib, Dasatinib, Desipramine, Dexmedetomidine, Dexmethylphenidate, Dextroamphetamine, d-Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine, Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

9. A composition consisting of:
one or more pharmacologically active agents provided in an amount that induce a cardiac channelopathy or a condition resulting from the irregularity or alteration in the cardiac pattern in a subject and one or more lipids provided in an amount sufficient to prevent or reduce the cardiac channelopathy or the condition resulting from the irregularity or alteration in the cardiac pattern caused by the one or more pharmacologically active agents in a formulation, wherein the formulation is dispersed in a pharmaceutically acceptable medium, solvent, or vehicle, wherein the active agent, the lipids, or both are dissolved, dispersed, or suspended in the medium, the solvent, or the vehicle, wherein the lipids form empty liposomes that reduce or prevent the cardiac channelopathy or a condition resulting from the irregularity or alteration in the cardiac pattern, wherein the active agent is selected from Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Curcumin, Crizotinib, Dabrafenib, Dasatinib, Desipramine, Dexmedetomidine, Dexmethylphenidate, Dextroamphetamine, d-Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine, Methylphenidate, Midodrine, Mifepristone, Mirabegron, Mirtazapine, Moexipril/HCTZ, Moxifloxacin, Nelfinavir, Nicardipine, Nilotinib, Norepinephrine, Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, and Ziprasidone.

10. The composition of claim 9, wherein the one or more pharmacologically active agents is selected from at least one of 5-HT3 antagonists that block serotonin binding, 5-HT4 receptor agonists, histamine antagonists, calcium channel blockers, anti-malarial agents, antipsychotic agents, halodols, antibiotics, anti-arrhythmics, anti-cancer agents, opioids, or hypolipidemic agents.

11. The composition of claim 9, wherein the lipid comprises at least one of a phosphatidylcholine, a phosphatidylethanolamine, a phosphatidylserine, a phosphatidylglycerol, a cardiolipin, a phosphatidylinositol or a precursor thereof.

12. The composition of claim 9, wherein the lipid comprises a lysophosphatidylglycerol, a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine, erucoyl-lysophosphatidylcholine, 1-Myristoyl-2-Hydroxy-sn-Glycero-3-Phosphocholine, 1,2-Dimyristoyl-sn-glycero-3-phosphorylcholine (DMPC), 1,2-Mysteroyl-2-Hydroxy-sn-Glycero-3-[Phospho-rac-(glycerol)], 1,2-Dimyristoyl-sn-glycero-3-phosphorylglycerol (DMPG), DMPC/DMPG, 1-myristoyl-2-hydroxy-sn-glycero-3-phospho-(1'-rac-glycerol) (LysoPG), or 1-myristoyl-2-hydroxy-sn-glycero-3-phosphocholine (LysoPC).

13. The composition of claim 9, wherein the cardiac channelopathy or the condition resulting from the irregularity or alteration in the cardiac pattern is prolongation of the QTc, LQT2, LQTS, or torsades de pointes.

14. The composition of claim 9, wherein the composition is adapted for enteral, parenteral, intravenous, intraperitoneal, cutaneous, subcutaneous, pulmonary, rectal, vaginal, or oral administration.

15. A composition consisting of:
one or more pharmacologically active agents provided in an amount that induce a cardiac channelopathy or a condition resulting from the irregularity or alteration in the cardiac pattern selected from QTc, LQT2, LQTS, and torsades de pointes in a subject and one or more lipids provided in an amount sufficient to prevent or reduce the cardiac channelopathy or the condition resulting from the irregularity or alteration in the cardiac pattern caused by the one or more pharmacologically active agents in an intravenous formulation, wherein the formulation is dispersed in a pharmaceutically acceptable medium, solvent, or vehicle, wherein the active agent, the lipids, or both are dissolved, dispersed, or suspended in the medium, the solvent, or the vehicle, wherein the active agent is selected from Albuterol, Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Curcumin, Crizotinib, Dabrafenib, Dasatinib, Desipramine, Dexmedetomidine, Dexmethylphenidate, Dextroamphetamine, d-Amphetamine, Dihydroartemisinin and Piperaquine, Diphenhydramine, Disopyramide, Dobutamine, Dofetilide, Dolasetron, Domperidone, Dopamine, Doxepin, Dronedarone, Droperidol, Ephedrine, Epinephrine, Adrenaline, Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide, Frusemide, Galantamine, Gatifloxacin, Gemifloxacin, Granisetron, Halofantrine, Haloperidol, Hydrochlorothiazide, Ibutilide, Iloperidone, Imipramine, Melipramine, Indapamide, Isoproterenol, Isradipine, Itraconazole, Ivabradine, Ketoconazole, Lapatinib, Levalbuterol, Levofloxacin, Levomethadyl, Lisdexamfetamine, Lithium, Mesoridazine, Metaproterenol, Methadone, Methamphetamine, Methylphenidate, Midodrine, Mifepristone, Mirabegron, Mirtazapine, Moexipril/HCTZ, Moxifloxacin, Nelfinavir, Nicardipine, Nilotinib, Norepinephrine, Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salbutamol, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, and Ziprasidone.

16. The composition of claim 15, wherein the one or more pharmacologically active agents is selected from at least one of 5-HT3 antagonists that block serotonin binding, 5-HT4 receptor agonists, histamine antagonists, calcium channel blockers, anti-malarial agents, antipsychotic agents, halodols, antibiotics, anti-arrhythmics, anti-cancer agents, opioids, or hypolipidemic agents.

17. The composition of claim 15, wherein the lipid comprises at least one of a phosphatidylcholine, a phosphatidylethanolamine, a phosphatidylserine, a phosphatidylglycerol, a cardiolipin, a phosphatidylinositol or a precursor thereof.

18. The composition of claim 15, wherein the lipid comprises a lysophosphatidylglycerol, a lysophosphatidylcholine, lauroyl-lysophosphatidylcholine, myristoyl-lysophosphatidylcholine, palmitoyl-lysophosphatidylcholine, stearoyl-lysophosphatidylcholine, arachidoyl-lysophosphatidylcholine, oleoyl-lysophosphatidylcholine, linoleoyl-lysophosphatidylcholine, linolenoyl-lysophosphatidylcholine, erucoyl-lysophosphatidylcholine, 1-Myristoyl-2-Hydroxy-sn-Glycero-3-Phosphocholine, 1,2-Dimyristoylsn-glycero-3-phosphorylcholine (DMPC), 1,2-Mysteroyl-2-Hydroxy-sn-Glycero-3-[Phospho-rac-(glycerol)], 1,2-Dimyristoyl-sn-glycero-3-phosphorylglycerol (DMPG), DMPC/DMPG, 1-myristoyl-2-hydroxy-sn-glycero-3-phospho-(1'-rac-glycerol) (LysoPG), or 1-myristoyl-2-hydroxy-sn-glycero-3-phosphocholine (LysoPC).

* * * * *